US011617848B2

(12) United States Patent
Fyfe et al.

(10) Patent No.: US 11,617,848 B2
(45) Date of Patent: *Apr. 4, 2023

(54) EXHALATION PORT

(71) Applicant: Fisher & Paykel Healthcare Limited, Auckland (NZ)

(72) Inventors: Katie Fyfe, Auckland (NZ); Kevin Blake Powell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 501 days.

This patent is subject to a terminal disclaimer.

(21) Appl. No.: 16/810,751

(22) Filed: Mar. 5, 2020

(65) Prior Publication Data
US 2020/0289781 A1    Sep. 17, 2020

Related U.S. Application Data

(63) Continuation of application No. 15/745,643, filed as application No. PCT/NZ2016/050101 on Jun. 27, 2016, now Pat. No. 10,632,276.

(Continued)

(51) Int. Cl.
*A61M 16/10* (2006.01)
*A61M 16/06* (2006.01)
*A61M 16/08* (2006.01)

(52) U.S. Cl.
CPC ........ *A61M 16/1065* (2014.02); *A61M 16/06* (2013.01); *A61M 16/0683* (2013.01);
(Continued)

(58) Field of Classification Search
CPC .............. A61M 16/00; A61M 16/0057; A61M 16/0066; A61M 16/06; A61M 16/0611;
(Continued)

(56) References Cited

U.S. PATENT DOCUMENTS 3,769,973 A    11/1973  Esbenshade
5,937,851 A *  8/1999  Serowski .......... A61M 16/0825
                                                   128/205.25
(Continued)

FOREIGN PATENT DOCUMENTS

CN         1893994 A       1/2007
WO    WO 2005/056091       6/2005
(Continued)

OTHER PUBLICATIONS

International Search Report and Written Opinion for PCT/NZ2016/050101 dated Oct. 20, 2016 in 17 pages.
(Continued)

*Primary Examiner* — Joseph D. Boecker
(74) *Attorney, Agent, or Firm* — Knobbe, Martens, Olson & Bear, LLP

(57) ABSTRACT

Several embodiments of exhalation ports for use respiratory systems are described. Some of the embodiments provide an elongate body defining a lumen through which gases may flow. A plurality of tapered openings is arranged on a portion of the elongate body and configured to vent gases. A shroud extends from the elongate body and surrounds one or more of the plurality of tapered openings. The exhalation port is arranged to removably connect in-line with a circuit for delivering gases to a patient.

16 Claims, 21 Drawing Sheets

Related U.S. Application Data

(60) Provisional application No. 62/328,458, filed on Apr. 27, 2016, provisional application No. 62/194,747, filed on Jul. 20, 2015.

(52) U.S. Cl.
CPC .... *A61M 16/0816* (2013.01); *A61M 16/0833* (2014.02); *A61M 16/0858* (2014.02); *A61M 2202/0225* (2013.01); *A61M 2205/42* (2013.01); *A61M 2205/583* (2013.01)

(58) Field of Classification Search
CPC .......... A61M 16/0622; A61M 16/0666; A61M 16/0672; A61M 16/0816; A61M 16/0833; A61M 16/085; A61M 16/0858; A61M 16/0883; A61M 16/1065; A61M 2205/42; A62B 18/02; A62B 18/025; A62B 18/04; A61B 5/082; A61B 5/087
See application file for complete search history.

(56) References Cited

U.S. PATENT DOCUMENTS

| 8,205,615 | B1 | 6/2012 | Ho |
| 10,632,276 | B2 * | 4/2020 | Fyfe .................. A61M 16/0833 |
| 2002/0029779 | A1 | 3/2002 | Schmidt et al. |
| 2004/0065327 | A1 | 4/2004 | Gradon et al. |
| 2008/0276937 | A1 | 11/2008 | Davidson et al. |
| 2009/0044810 | A1 | 2/2009 | Kwok et al. |
| 2013/0010769 | A1 | 6/2013 | Kang et al. |
| 2013/0160769 | A1 | 6/2013 | Ng et al. |
| 2016/0271351 | A1 * | 9/2016 | Frater ............... A61M 16/0057 |

FOREIGN PATENT DOCUMENTS

| WO | WO 2009/093977 | 7/2009 |
| WO | WO 2009/136333 | 11/2009 |
| WO | WO 2011/080604 | 7/2011 |
| WO | WO 2011/142678 | 11/2011 |
| WO | WO 2012/109704 | 8/2012 |
| WO | WO 2014/129913 | 8/2014 |
| WO | WO 2015/048849 | 4/2015 |
| WO | WO 2017/014647 | 1/2017 |

OTHER PUBLICATIONS

International Preliminary Report on Patentability for PCT/NZ2016/050101 dated Jan. 23, 2018 in 13 pages.

* cited by examiner

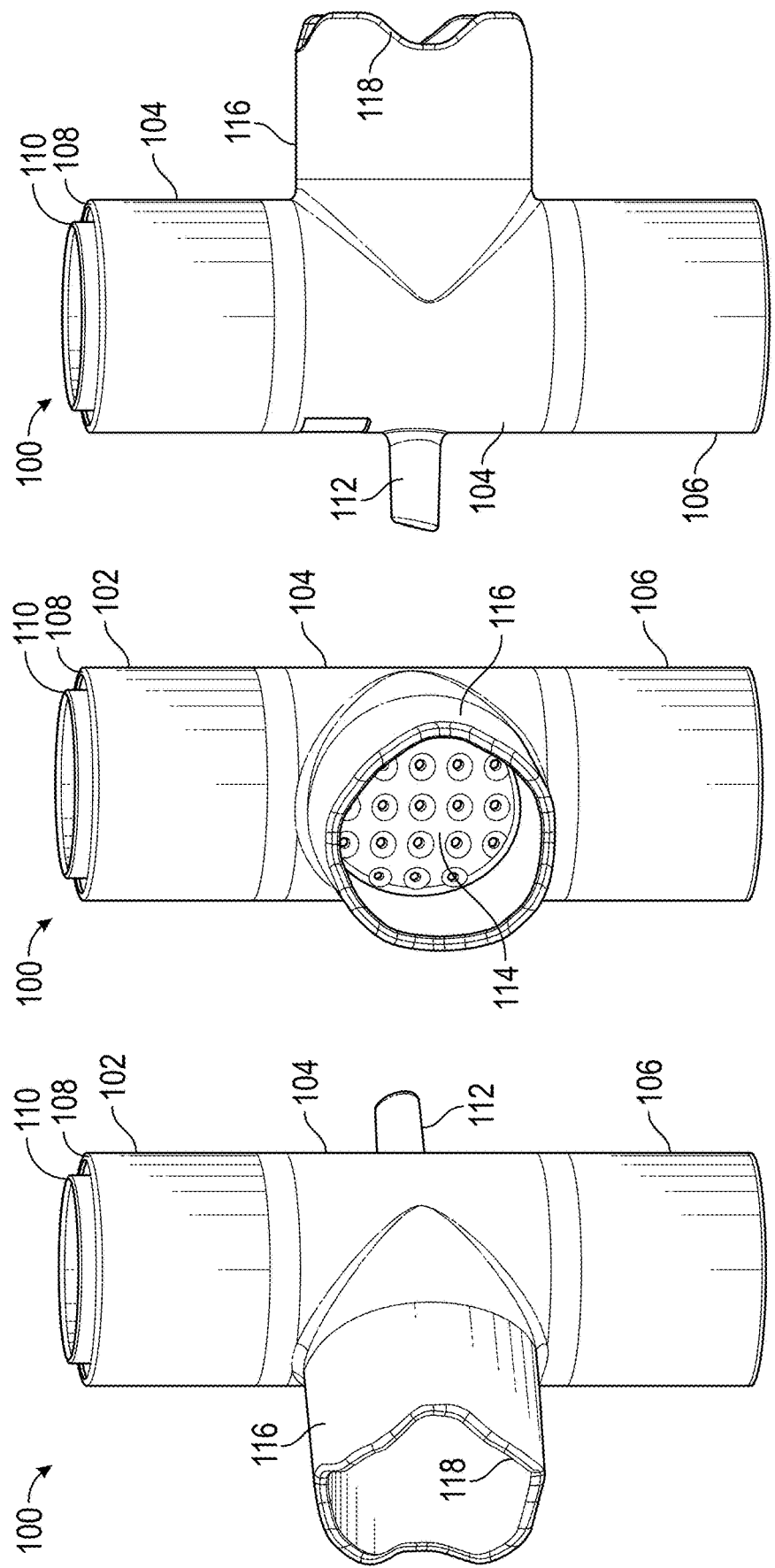

EXHALATION PORT

INCORPORATION BY REFERENCE TO ANY PRIORITY APPLICATIONS

This application is continuation of U.S. patent application Ser. No. 15/745,643, filed Jan. 17, 2018, which is a national stage application based on International Application No. PCT/NZ2016/050101, filed Jun. 27, 2016, which claims the priority benefit of U.S. Provisional Application No. 62/328,458, filed Apr. 27, 2016, and 62/194,747, filed Jul. 20, 2015. Any and all applications for which a foreign or domestic priority claim is identified in the Application Data Sheet as filed with the present application are hereby incorporated by reference under 37 CFR 1.57.

BACKGROUND

Field of the Invention

The present disclosure generally relates to exhalation ports for respiratory interfaces. More particularly, the present disclosure relates to exhalation ports used in single-limb, noninvasive ventilation systems.

Description of the Related Art

Noninvasive ventilation (NIV) is the delivery of respiratory support without using an invasive artificial airway such as an endotracheal tube. Noninvasive positive pressure ventilation can be implemented using a mechanical ventilator connected by tubing to a mask that directs airflow into the patient's nose or the nose and mouth. Head straps are used to secure the mask to the patient. Use of single-limb, positive-pressure ventilation delivered through a mask is a recognized method for providing noninvasive respiratory support to patients, and is an integral tool in the management of both acute and acute on chronic respiratory failure.

An exhalation port is used to evacuate a patient's exhaled gasses from a single-limb, NIV breathing circuit when a non-vented mask is used. During exhalation, the patient's exhaled gases flow out of the exhalation port located in-line with the breathing circuit at the connection between the mask and the air flow conduit. In use, the exhaled gases are pushed through the port by the incoming gases at therapeutic pressure rates sufficient to keep rebreathing of carbon dioxide ($CO_2$) at acceptable levels. Improvements to exhalation ports are desired to reduce draft from the exhalation port, to reduce noise of exhaled gas exiting the exhalation port, and to provide the ability to filter the exhaled gas.

SUMMARY

According to a first aspect of the disclosure, there is provided an exhalation port device for use with a single-limb noninvasive ventilation apparatus which conveys gases along a gases pathway and delivered to a patient via a mask, where the exhalation port device comprises an elongate body that is hollow and defines a lumen to carry a flow of gases; a plurality of openings arranged on a portion of the elongate body, the openings configured to vent gases through the openings; a shroud extending from the elongate body, the shroud surrounding one or more of the plurality of openings; wherein the plurality of openings are tapered; and wherein the exhalation port is arranged to removably connect in-line with a circuit for delivering gases to a patient.

In some embodiments the shroud extends outward from the elongate body.

In some embodiments the shroud extends outward from the elongate body in a substantially annular form.

In some embodiments the shroud extends outward from the elongate body approximately normal to the elongate body.

In some embodiments the shroud extends outward from the elongate body at an angle of between approximately 30 degrees and approximately 45 degrees.

In some embodiments the shroud extends outward from the elongate body at an angle of between approximately 120 degrees and approximately 135 degrees.

In some embodiments the shroud has a wall which extends outward from the elongate body and an internal portion of the wall is tapered inwardly, the taper extending from a portion of the shroud adjacent the elongate body to an outside surface of the shroud, the taper being at an angle between approximately 1 degree and approximately 8 degrees.

In some embodiments the shroud has an outside surface, and the outside surface has a 22 mm taper configured to removably connect with a filter.

In some embodiments the shroud has an outside surface, and the outside surface has a 15 mm taper configured to removably connect with a filter.

In some embodiments the shroud has an outside surface, and the outside surface of the shroud has a plurality of notches.

In some embodiments the plurality of notches are spaced equally around the outside surface of the shroud.

In some embodiments each of the plurality of notches comprises a notch dimension and a spacing dimension.

In some embodiments each of the plurality of notches comprises a notch dimension that is substantially equal to the spacing dimension.

In some embodiments each of the plurality of notches comprises a notch dimension that is substantially greater than the spacing dimension.

In some embodiments the shroud has an outside surface, and the outside surface of the shroud is substantially planar.

In some embodiments the shroud is offset and extends at an angle to the elongate body.

In some embodiments the shroud is hingedly attached to the elongate body.

In some embodiments the shroud is removable from the elongate body.

In some embodiments the elongate body further comprises a first end, wherein the first end of the elongate body comprises a 22 mm male taper and a 15 mm female taper nested within the 22 mm male taper.

In some embodiments the shroud has a wall and the wall has a plurality of slots.

In some embodiments the plurality of slots are substantially oval.

In some embodiments the plurality of slots are substantially circular.

In some embodiments the shroud has an outer wall and the outer wall has alternating recessed strips and ridges around a circumference of the outer wall.

In some embodiments the shroud has an outer wall and an outer surface, the outer wall having alternating recessed strips and ridges around a circumference of the outer wall, the outer surface having a plurality of notches, and the recessed strips and the notches are aligned.

In some embodiments the exhalation port includes a filter connector adaptor configured to connect the shroud with alternating recessed strips and ridges to filter.

In some embodiments the shroud has a free portion that is substantially annular and wherein the substantially annular free portion of the shroud comprises at least one slot.

In some embodiments the plurality of slots are substantially radially positioned on the wall of the shroud.

In some embodiments the plurality of slots are substantially axially positioned on the wall of the shroud.

In some embodiments each of the plurality of openings is tapered such that it is widest on an external surface of the opening.

In some embodiments each of the plurality of openings has a diameter at an internal surface of the opening, a radius at an external surface of the opening, and a depth.

In some embodiments for each of the plurality of openings the diameter at an internal surface of the opening is between approximately 0.4 mm and approximately 1 mm.

In some embodiments for each of the plurality of openings the radius at an external surface of the opening is between approximately 0.4 mm and approximately 1.0 mm.

In some embodiments for each of the plurality of openings the depth is at least two times the diameter at an internal surface of the opening.

In some embodiments each of the plurality of openings has a center, and wherein the exhalation port further comprises a pitch distance for each of the plurality of openings, the pitch distance being a distance between the center of a first opening and the center of those of the plurality of openings that are adjacent to the first opening.

In some embodiments each of the plurality of openings has a diameter, and the pitch distance for each of the plurality of openings is at least four times the diameter.

In some embodiments the diameter is between approximately 0.4 mm and approximately 1 mm.

In some embodiments the plurality of openings are arranged in an offset pattern within the shroud.

In some embodiments the offset pattern is such that each opening is offset from each other opening.

In some embodiments one of the plurality of openings is a central opening and a remainder of the plurality of openings are arranged in a circular pattern within the shroud such that the remainder of the plurality of openings extend in at least one circular arrangement around the central opening.

In some embodiments the plurality of openings are arranged in a square pattern such that each opening is aligned with an adjacent opening.

In some embodiments the plurality of openings comprises between 15 and 37 openings arranged in a square pattern such that each opening is aligned with an adjacent opening.

In some embodiments the plurality of openings comprises 21 openings arranged in a square pattern such that each opening is aligned with an adjacent opening.

In some embodiments the exhalation port includes a removably attachable filter that can be removably attached to the shroud.

In some embodiments the removably attachable filter is a sintered plastic filter.

In some embodiments the exhalation port includes a filter that is permanently attachable to the plurality of openings.

In some embodiments the exhalation port includes a filter that is permanently attachable to the shroud.

In some embodiments the exhalation port includes a filter that is a cap that is removably placeable in the shroud.

In some embodiments the exhalation port includes a filter that is a disk made of sintered plastic that is removably placeable in the shroud.

In some embodiments the exhalation port includes a filter that is a diffuser that is removably placeable in the shroud.

In some embodiments the exhalation port includes a filter that is integrated around the plurality of openings onto the elongate body, and wherein the filter also includes a hole defining a gases passageway.

In some embodiments the exhalation port includes a filter that is a membrane disk that is positioned within two parts.

In some embodiments the exhalation port includes a pressure port extending outward from the elongate body, the pressure port configured to couple with a pressure sampling line that connects to a noninvasive ventilator.

According to a another aspect of the disclosure, there is provided a noninvasive ventilation mask system for use with a single-limb noninvasive ventilation apparatus which conveys gases along a gases pathway and delivered to a patient via a noninvasive ventilation mask, where the noninvasive ventilation mask system comprises:

a cushion module having a rigid body and a soft seal attached to the rigid body;

a rigid frame having at least two headgear connectors;

a swiveling elbow connectable to the cushion module or to the rigid frame; and an exhalation port removably connectable to the elbow.

Preferably the soft seal comprises a rolling hinge portion at the nasal bridge.

Preferably the noninvasive ventilation mask system includes a headgear arrangement comprising a pair of upper strap portions, each upper strap portion positioned on opposing sides of a patient's head, a crown strap extending between the two upper strap portions, the crown strap extending across a crown of the patient's head.

Preferably the exhalation port further comprises:

an elongate body, said elongate body defining a lumen to carry a flow of gases;

a plurality of holes arranged on a portion of the elongate body, the holes configured to vent gases;

a shroud extending from the elongate body, the shroud surrounding one or more of the plurality of holes;

wherein the plurality of holes are tapered; and wherein the exhalation port is arranged to removably connect to the swiveling elbow and to a circuit for delivering gases to the patient.

Further aspects of the present disclosure, which should be considered in all its novel aspects, will become apparent to those skilled in the art upon reading of the following description which provides at least one example of a practical application of the present disclosure.

BRIEF DESCRIPTION OF THE DRAWINGS

Various embodiments of the present disclosure will now be described, by way of illustrative example only, with reference to the accompanying drawings. In the drawings, similar elements have the same reference numerals.

FIGS. 3A and 3B are perspective views of an exhalation port in accordance with an embodiment of the present disclosure.

FIG. 3C is a side view of the embodiment of the exhalation port of FIGS. 3A and 3B.

DETAILED DESCRIPTION

Embodiments of the present disclosure include an exhalation port for use with, among other things, a single-limb, noninvasive ventilation (NIV) system. The disclosed embodiments are used to evacuate a patient's exhaled gasses from a breathing circuit. During exhalation, the patient's exhaled gases flow out of the exhalation port located in-line between the patient interface device (e.g., a mask) and the air flow conduit from the ventilator or gases source. In use, the exhaled gases are pushed through vent openings, or holes, in the port by the incoming gases at therapeutic pressure rates sufficient to keep rebreathing of carbon dioxide ($CO_2$) at acceptable levels.

Figure 1:
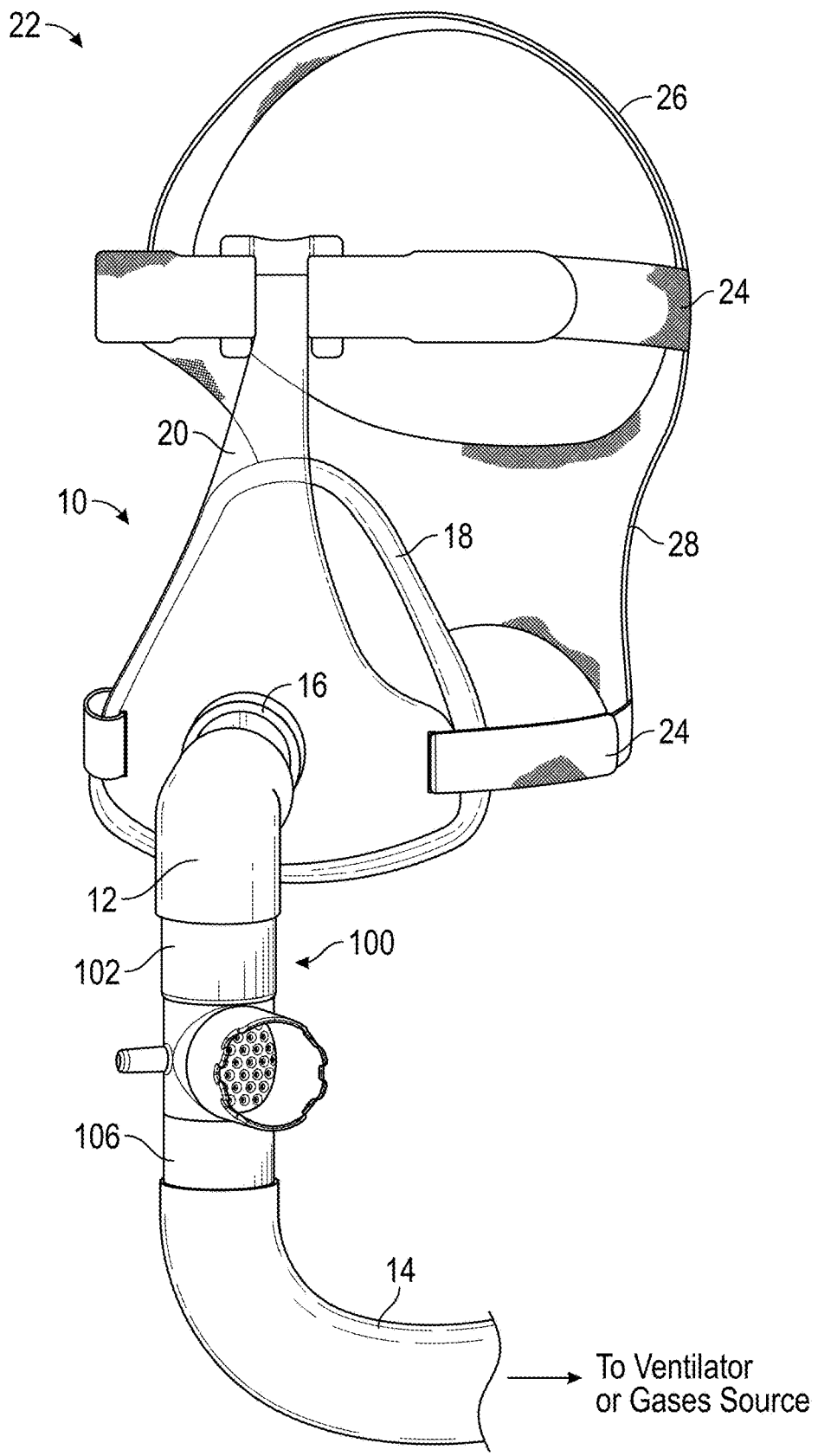
FIG. 1 is a perspective view of a mask with an attached exhalation port in accordance with an embodiment of the present disclosure.

Referring to FIG. 1, illustrated is a perspective view of a mask 10 with an exhalation port 100 attached in accordance with an embodiment of the present disclosure. The exhalation port 100 is attached to the elbow connector 12 of the full face mask 10. In some embodiments, the exhalation port 100 can be used with other types of patient interfaces, such as pillow masks, oral masks, oral-nasal masks, nasal masks, and the like. In the illustrated configuration, the exhalation port 100 is disposed in-line with a gases conduit 14, such that the exhalation port 100 has a first end 102 that is in fluid communication with an inlet 16 to the mask 10 and a second end 106 that is in fluid communication with a ventilator or gases source via a gases conduit 14. The exhalation port 100 is preferably attached to the elbow connector 12 at or near the inlet 16 of the mask 10. Positioning the exhalation port 100 close to the mask inlet 16 beneficially reduces the amount of dead space where CO2 gases can accumulate and beneficially reduces the rebreathing of exhaled gases by the patient.

Figure 2A:
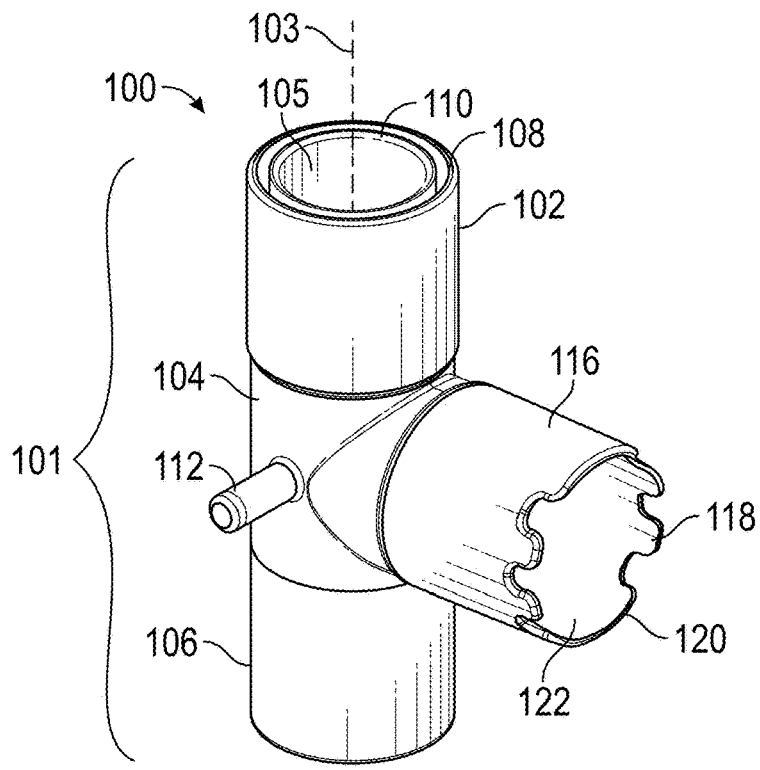
FIGS. 2A and 2B are perspective views of an exhalation port in accordance with an embodiment of the present disclosure.
Figure 2B:
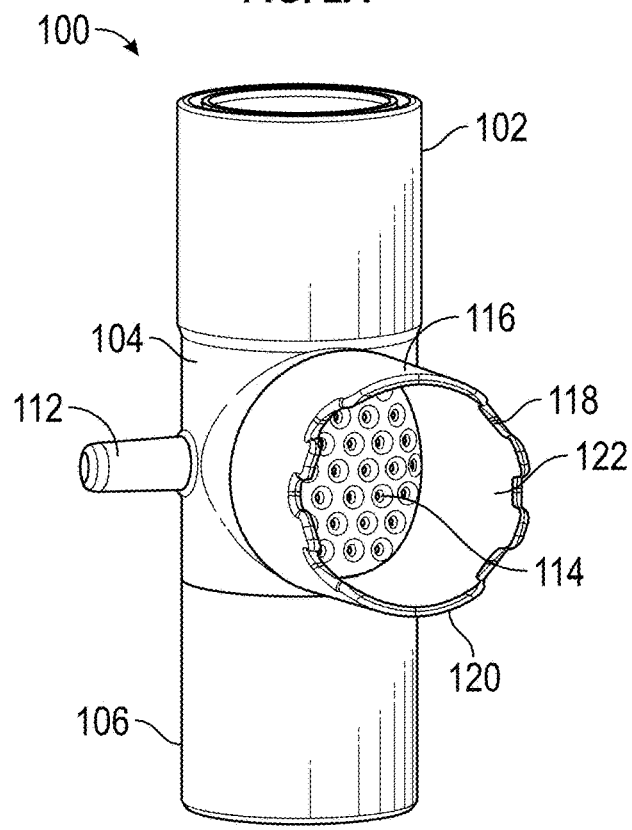
Figure 7:
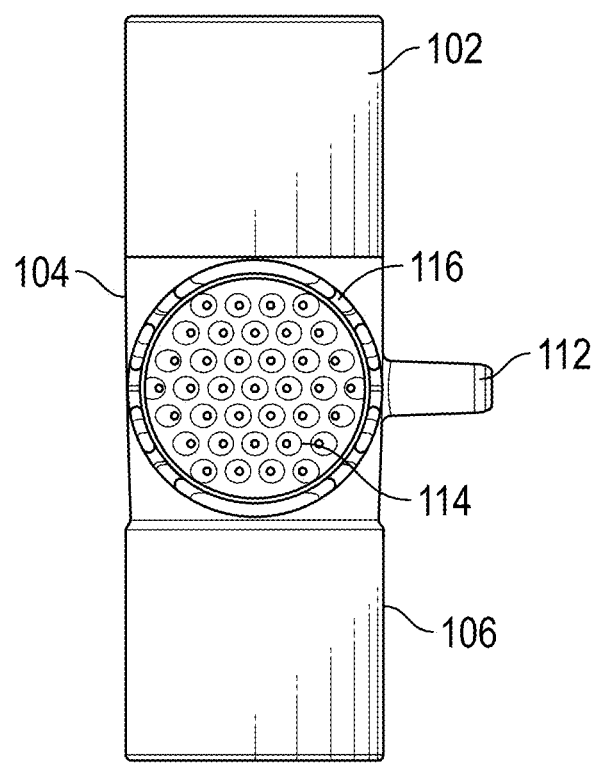
FIG. 7 is a front view of an exhalation port in accordance with an embodiment of the present disclosure.
Figure 8:
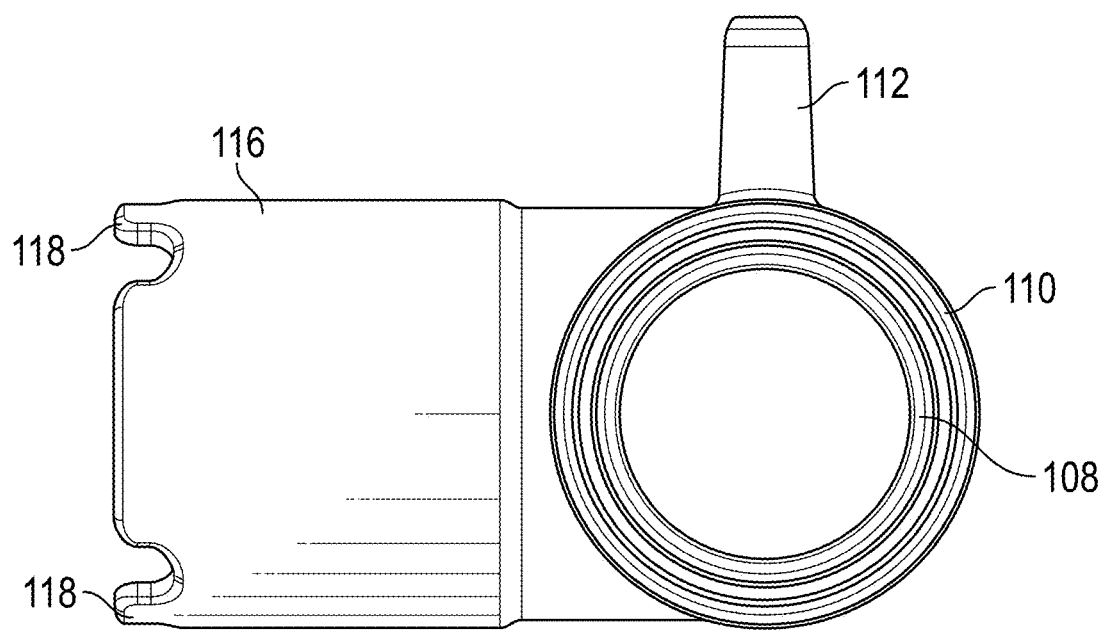
FIG. 8 is a top view of an exhalation port in accordance with an embodiment of the present disclosure.
Figure 9:
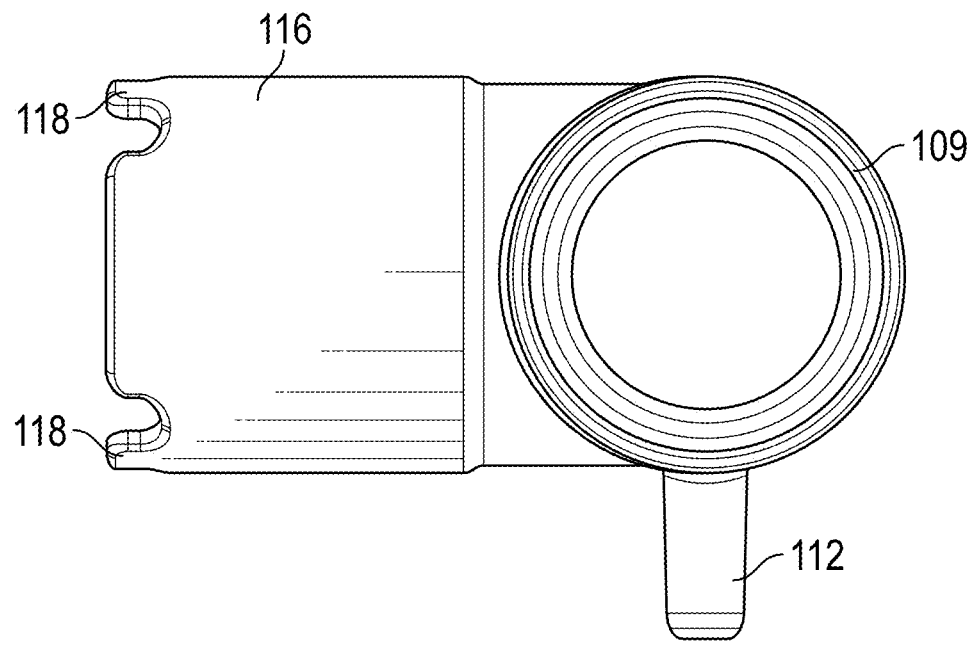
FIG. 9 is a bottom view of an exhalation port in accordance with an embodiment of the present disclosure.

FIGS. 2A and 2B show perspective views of an exhalation port 100 in accordance with an embodiment of the present disclosure, and FIGS. 7, 8 and 9 illustrate front, top and bottom views, respectively, of the embodiment 100. As shown in FIG. 2A, the exhalation port 100 includes an elongate body 101 having a hollow portion extending through a longitudinal axis 103 of the exhalation port 100, defining a lumen 105 through which gases may flow. The exhalation port 100 includes a top portion 102, a center portion 104, and a bottom portion 106.

Preferably the exhalation port 100 is constructed of a relatively inflexible material such as, for example, polycarbonate plastic. Such a material can provide the requisite rigidity. Advantageously, polycarbonate provides transparency permitting clinicians to see inside the exhalation port 100 for secretions or blockages that might form. Polycarbonate also delivers good dimensional stability. Other materials known in the art can be used to realize the disclosed exhalation port 100, including without limitation, polypropylene and Polyethylene Terephthalate Glycol-Modified (PETG).

The top portion 102 includes a 22 mm male taper 108 and 15 mm female taper 110 nested within the 22 mm male taper 108 to enable connection to various patient interfaces, such as, for example, the elbow connector 112 of the mask 10. The 15 mm female taper 110 can be used to connect to a tracheostomy tube. Other connection formats can be included in embodiments of the disclosed exhalation port 100 as well. For example, the outside surface 120 of the of the shroud 116 may include a proprietary connector configured to allow one or more proprietary external filters to be connected to the exhalation port 100. Additionally, at least one of the top portion 102 and bottom portion 106 can have a proprietary connection configured to mate with a proprietary elbow connector 112 to help ensure that exhalation ports 100 and masks 10 offered by the same manufacturer can be used together at the exclusion of other manufacturers' products. The bottom portion 106 includes a 22 mm male taper 109 (shown in FIG. 9) to connect to the gases conduit 14. The center portion 104 includes a ⅛ inch pressure line port 112 to couple with a pressure sampling line that connects to the noninvasive ventilator or gases source. When the pressure line port 112 is not in use, it may be closed off with a cap (not shown).

The center portion 104 of the exhalation port 100 also includes a plurality of vent holes 114 (also referred to herein as "openings 114") through which the patient's exhaled gases can be evacuated from the breathing circuit. A shroud 116 is positioned over and around the vent holes 114 to reduce draft from the exhaled gas. The shroud 116 is substantially annular. The shroud 116 allows venting of the exhaled gases and prevents blockage of the vent holes 114. Illustratively, the shroud 116 prevents entrainment of surrounding ambient air within the exhalation stream through the vent holes 114. The shroud 116 also has a 22 mm male taper at an outside surface 120 providing structure to which an external filter 170, 172 (shown in FIGS. 15A-15D) can be attached. The external filter 170, 172 prevents exposure to clinicians and others in proximity of the patient to infectious agents that may be in the patient's exhaled gases. Thus, the filter 170, 172 reduces the chance of infections spreading due to sick patients exhaling in a hospital setting.

The shroud 116 has an inner wall 122 that extends outward from the center portion 104 of the exhalation port 100. In accordance with certain embodiments, the inner wall 122 of the shroud 116 is tapered centrally. The taper extends from a portion of the shroud adjacent the elongate body to the outside surface 120 of the shroud 116 at an angle between 0 degrees and 8 degrees. In some embodiments the shroud is not tapered centrally.

The shroud 116 can include notches 118 which can reduce the chance of missuse by differentiating the shroud 116 from a wye-piece or T-piece so the shroud's taper is not used in a dual-limb NIV circuit. The notches 118 also reduce the probability of accidentally blocking the exhalation path. As illustrated in the embodiment disclosed in FIGS. 2A and 2B, the notches 118 are positioned on the outside surface 120 of the shroud 116. The dimensions, spacing, and number of the notches 118 can vary. For example, as illustrated in FIGS. 2A and 2B, the notches 118 are positioned diametrically opposite each other on portions of the outside surface 120 of the shroud 116.

Figure 14B:
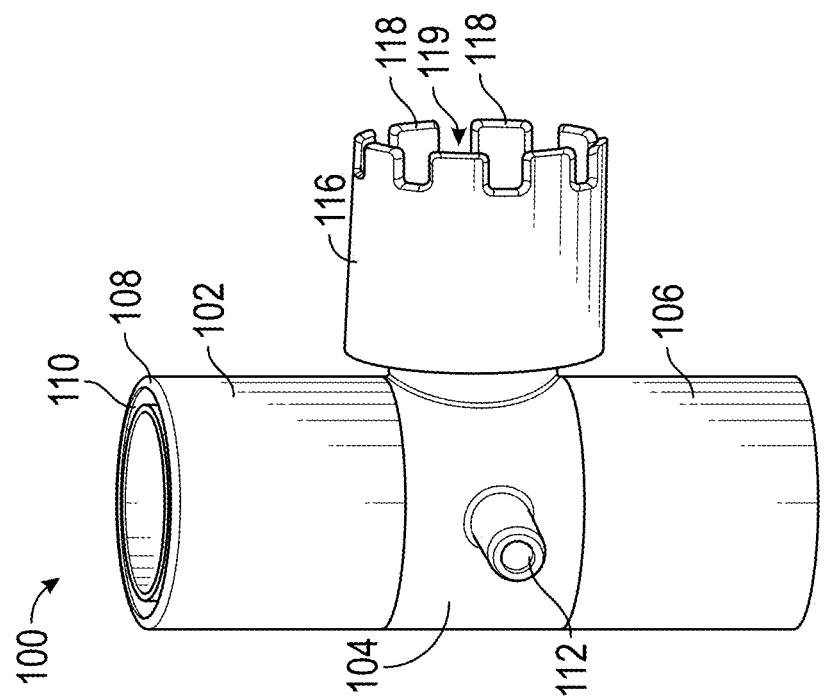
FIGS. 14A-14D are perspective views of tapers for an external filter in accordance with embodiments of the present disclosure.

Illustrated in FIGS. 3A-3C, is a preferred embodiment of the exhalation port 100 in which the shroud 116 includes four equally-spaced notches 118, having a rounded spacing between them. In some embodiments (as illustrated in FIGS. 14B and 14C), the notches 118 are spaced equally around the outside surface 120 of the shroud 116, and the dimensions of the notches 118 are substantially equal to the spacing dimensions between the notches 118. In certain embodiments, the notches 118 have a dimension that is substantially greater than the dimension of the spacing between the notches 118. Many other forms and variations of notch 118 dimension, arrangement, and spacing can be used.

Figure 6:
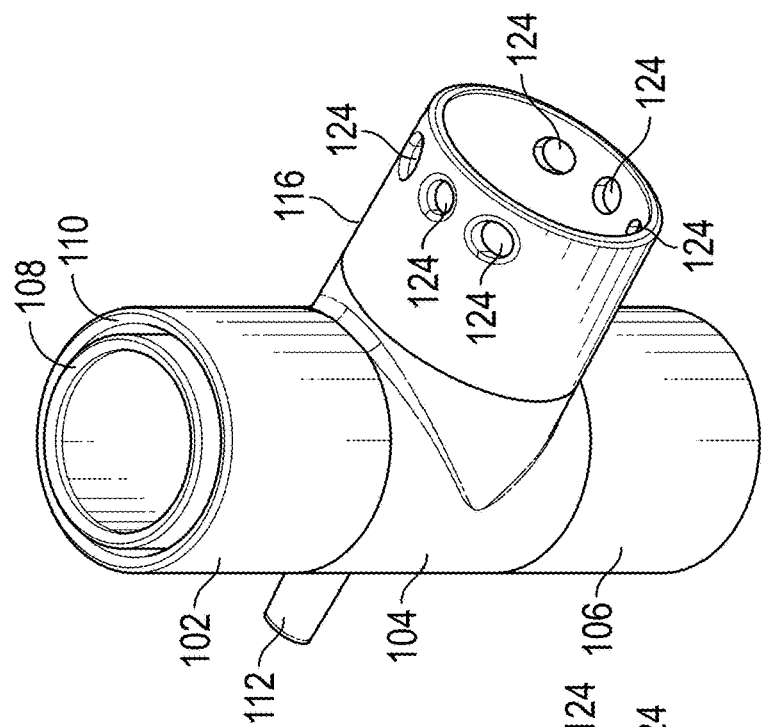
FIG. 6 is a perspective view of an exhalation port in accordance with an embodiment of the present disclosure.
Figure 5:
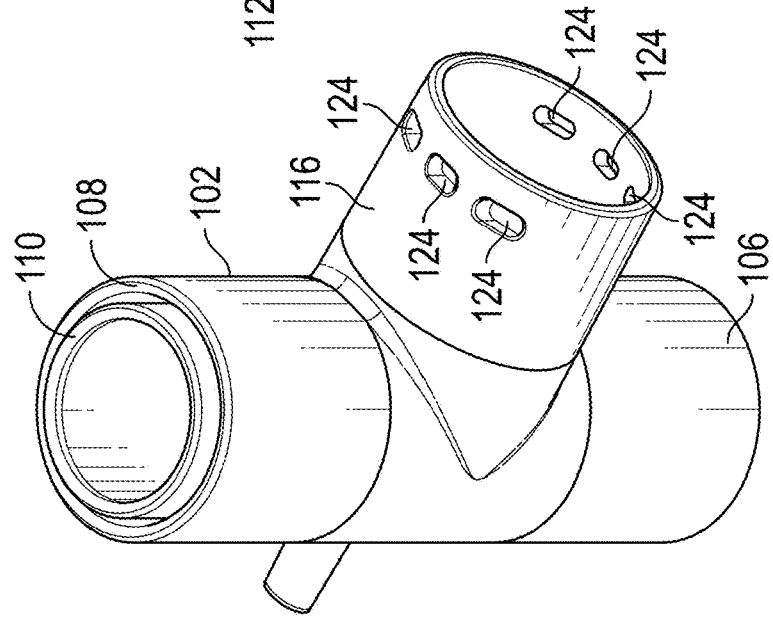
FIG. 5 is a perspective view of an exhalation port in accordance with an embodiment of the present disclosure.
Figure 4:
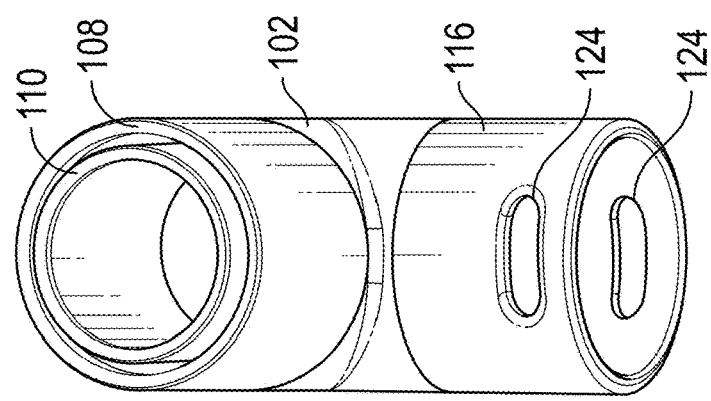
FIG. 4 is a perspective view of an exhalation port in accordance with an embodiment of the present disclosure.

FIGS. 4, 5, and 6 illustrate embodiments of the exhalation port 100 that employ slots 124 on the shroud 116. Like the notches 118, the slots 124 help prevent the vent holes 114 from being blocked. The slots 124 also allow venting of exhaled gases to the surrounding environment, and they serve to reduce the chance of inappropriate use of the exhalation port 100 by differentiating the shroud 116 to indicate that it is not to be used in a dual-limb NIV breathing circuit. The slots 124 also reduce the probability of accidentally blocking the exhalation path. The slots 124 can be in any form or shape, such as, for example, round or oval, and their orientation can be radially positioned around the surface of the shroud 116, axially positioned, directed toward the center portion 104, or positioned in any other orientation on the shroud 116. The slots 124 are preferably sufficiently close to the outside surface 120 of the shroud 116 such that they can be covered by a 22 mm female taper connection of an external filter 170, 172 (as shown in FIGS. 15A-15D) to prevent unfiltered exhaled gases from being released into the surrounding environment. In certain embodiments, the slots 124 extend vertically or axially along the outside wall of the shroud 116. In such embodiments, standard external filters 170, 172 may not completely cover the slots 124; however, proprietary external filters may be configured to mate with the shroud 116 so as to completely cover the vertically extended slots 124.

FIGS. 21A-24 illustrate embodiments of the exhalation port 100 that employ leak paths 126 on the shroud 116 by having a plurality of alternating recessed strips 125 and ridges 128 on the wall of the shroud 116. The recessed strips 125 and the ridges 128 can start from the outer surface 120 of the shroud 116 and extend toward the centre portion 104. The recessed strips 125 and/or the ridges 128 can reach the centre portion 104 or stop between the outer surface 120 of the shroud 116 and the centre portion 104. Like the notches 118 and the slots 124 described above, the leak paths 126 help prevent the vent holes 114 from being blocked when an opening defined by the outer surface 120 of the shroud 116 is covered up by mistake. For example, the shroud 116 can be covered up when a 22 mm female cap (not shown) or a nebulizer (not shown) is mistakenly connected to the 22 mm male taper at the outside surface 120 of the shroud 126. The shroud 116 can also be covered up when the external filter 170, 172 (as shown in FIGS. 15A-15D) that is connected to the 22 mm male taper at the outside surface 120 of the shroud 116 becomes blocked or clogged. For example, the filter 170, 172 can become clogged with particulate matters. The leak paths 126 allow the exhaled gases to be expired or leaked out via the leak paths 126 formed in the shroud 116. Allowing the exhaled gases to escape from the leak paths 126 can reduce the amount of dead space where $CO_2$ gases can accumulate, reduce the build-up of $CO_2$ gases in the mask, and beneficially reduce the rebreathing of exhaled gases by the patient. In the illustrated embodiment, the coupling between the 22 mm female connection of the cap, the nebulizer, or the external filter 170, 172, and the 22 mm male taper at the outer surface 120 of the shroud 116 is not airtight. An inner wall of the 22 mm female connection of the cap, the nebulizer, or the external filter 170, 172, can contact an outer wall of the ridges 128, resulting in the leak paths 126 being formed between the inner wall of the 22 mm female connection of the cap, the nebulizer, or the external filter 170, 172, and an outer wall of the recessed strips 125. The exhaled gases from the vent holes 114 can escape to the surrounding environment through the leak paths 126 to reduce the amount of dead space where $CO_2$ gases can accumulate and the build-up of $CO_2$ gases in the mask so that the patient will not rebreathe too much $CO_2$ when the shroud 116 is covered up in circumstances described above. The alternating recessed strips 125 and ridges 128 also serve to reduce the chance of inappropriate use of the exhalation port 100 by differentiating the shroud 116 from a regular 22 mm male taper to indicate that it is not to be used in a dual-limb NIV breathing circuit.

The leak paths 126 can be formed in variety of ways. In some embodiments, the recessed strips 125 can be formed by cutting out portions of an outer wall of the shroud 116. In some embodiments, the ridges 128 can be affixed to the outer wall of the shroud 116 by, for example, adhesives, welding, or other methods known in the art. In some embodiments, the exhalation port 100 is formed by a molding operation. Similarly, the recessed portions 125 and the ridges 128 can also be formed by the molding operation using an appropriately shaped tool used to mold the exhalation port 100. The exhalation port can be molded from any appropriate thermoplastic, such as polycarbonate.

The dimension, spacing and number of the leak paths 126 can vary. In some embodiments, the leak paths 126 can have a depth of about 0 mm to about 1.2 mm. In some embodiments, the leak paths 126 can have a depth of about 0.3 mm to about 0.9 mm. In some embodiments, the leak paths 126 can have a depth of about 0.6 mm. Sizes of the leak paths 126 can be tailored depending on whether there is a heightened need for filtering the exhaled gases. When there is less concern with the exhaled gases being infectious, wider and/or deeper recessed strips 125 may be formed on the shroud 116 so that more exhaled gases can leave from the leak paths 126 without being filtered. When there is more concern with the exhaled gases being infectious, narrower and/or less deep recessed strips 125 can be formed on the shroud 116 so that less exhaled gases can leave from the leak paths 126 without being filtered. The recessed strips 125 and/or the ridges 128, and thus the leak paths 126, can be of substantially the same shape, size and/or area, or different shapes, sizes and/or areas. The leak paths 126 can have a straight or tortuous path along a length of the shroud 116. A straight path may advantageously reduce airflow resistance of the exhaled gases through the leak paths 126. A straight path can also be cheaper to manufacture. A tortuous path can provide higher airflow resistance when it is desired that more exhaled gases be filtered through the filter 170, 172.

Figure 21B:
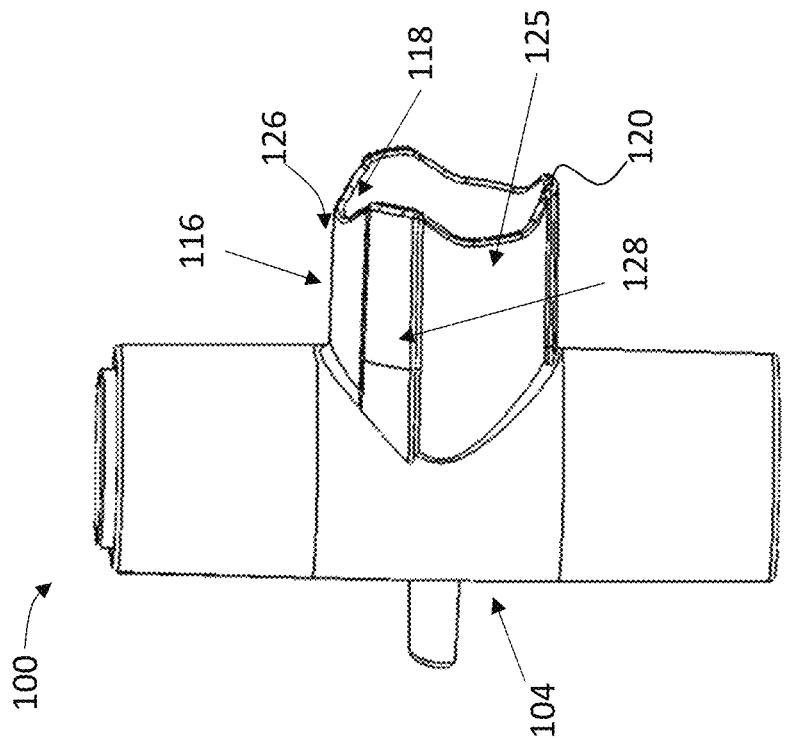
FIGS. 21A and 21B are perspective views of an exhalation port in accordance with an embodiment of the present disclosure.
Figure 21A:
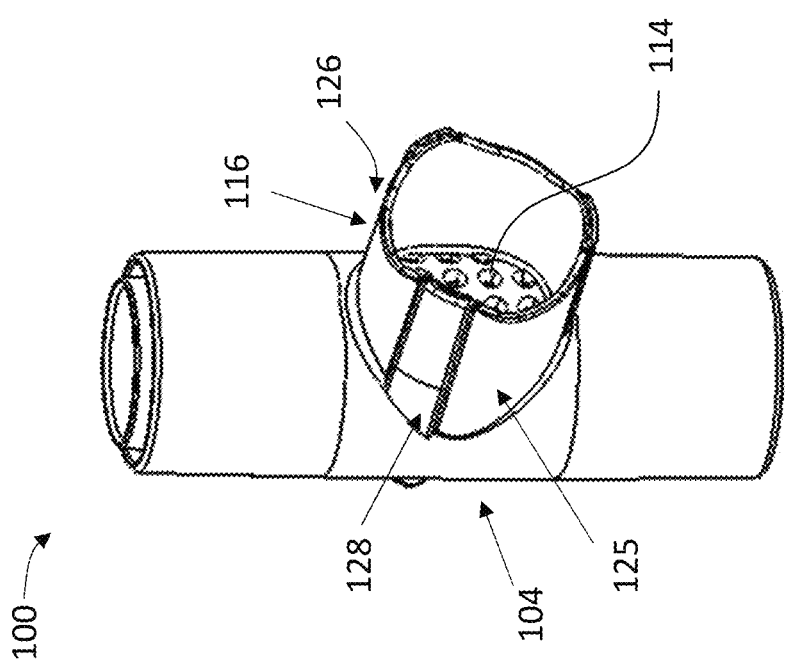
Figure 22B:
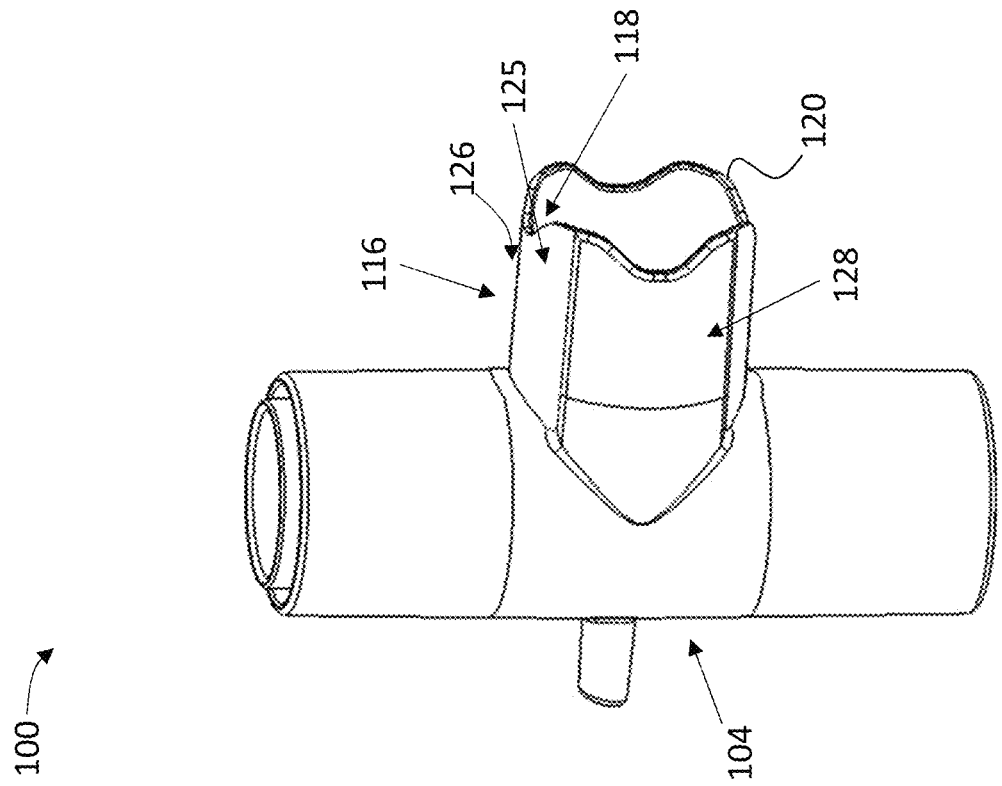
FIGS. 22A and 22B are perspective views of an exhalation port in accordance with an embodiment of the present disclosure.
Figure 22A:
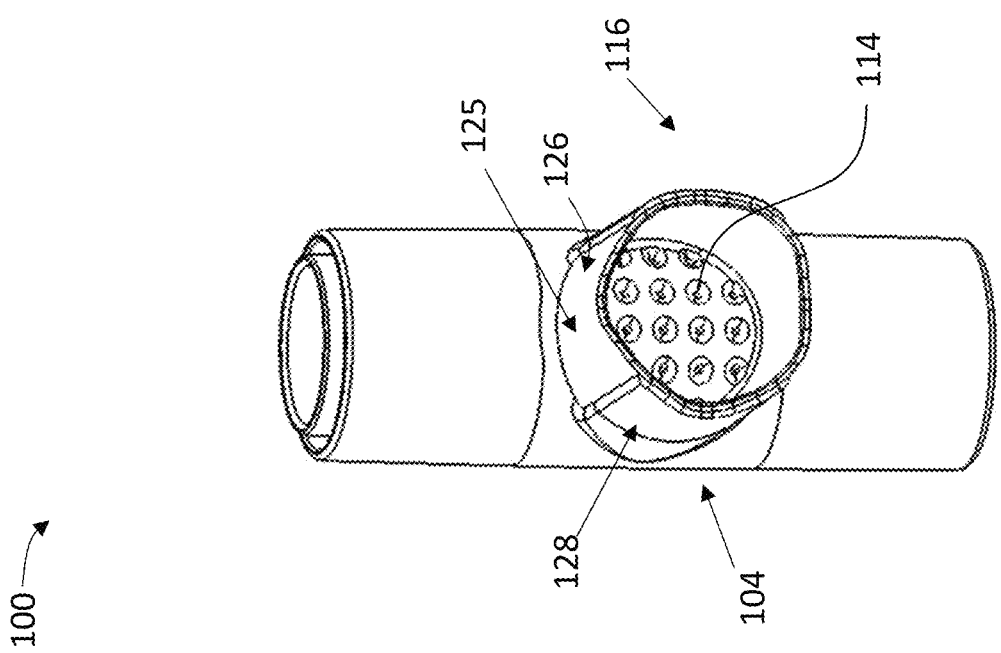
Figure 24:
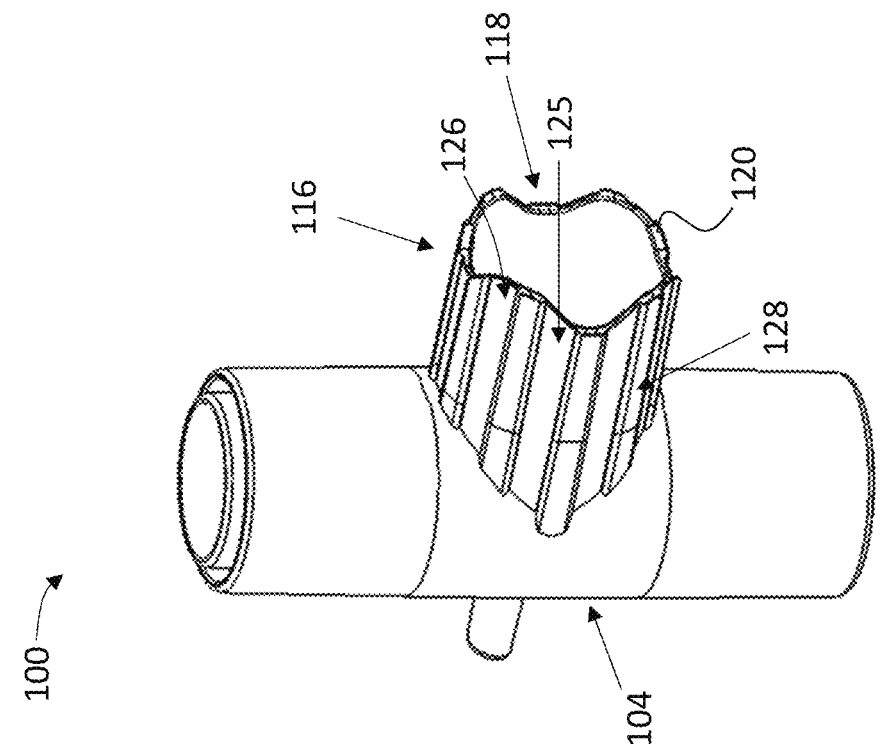
FIG. 24 is a perspective view of an exhalation port in accordance with an embodiment of the present disclosure.
Figure 23:
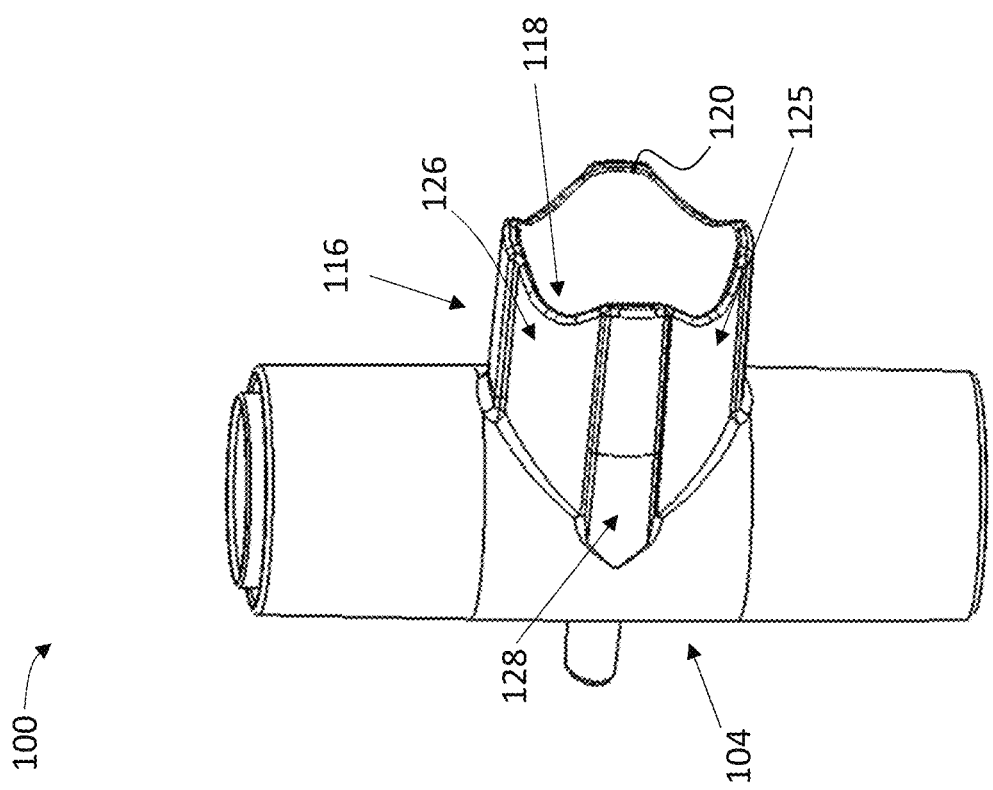
FIG. 23 is a perspective view of an exhalation port in accordance with an embodiment of the present disclosure.

As shown in FIGS. 21A and 21B, the shroud can have three recessed strips 125 alternating with three ridges 128. As shown in FIGS. 22A and 22B, the shroud can have two recessed strips 125 alternating with two ridges 128. As shown in FIG. 23, the shroud can have four recessed strips 125 alternating with four ridges 128. As shown in FIG. 24, the shroud can have more than four recessed strips 125 alternating with more than four ridges 128. A higher number of the leak paths 126 can advantageously produce more stable connection between the shroud 116 and the filter 170, 172 because points of contact between the ridges 128 and the filter 170, 172 can be more spread out around the circumference of the shroud 116. A lower number of the leak paths 126, on the other hand, can be manufactured more cheaply than the higher number of the leak paths 126.

The leak paths 126 can be equally spaced around the circumference of the shroud 116, or have varying spacings around the circumference of the shroud 116. Equal spacing of the leak paths 126 may advantageously provide more stable connection between the shroud 116 and the filter 170, 172. Equal spacing of the leak paths may also advantageously produce more uniform airflow through individual leak paths.

As shown in FIGS. 21A to 24, in some embodiments the shroud 116 also has a plurality of notches 118. Some or all of leak paths 126 and some or all of the notches 118 can be aligned. Aligning the leak paths 126 and the notches 118 can advantageously result in the shorter leak paths 126 than when the leak paths 126 align with a portion of the outer surface 120 that does not have the notches 118. The shorter leak paths 126 can produce less resistance for the exhaled gases to escape through the leak paths 126.

Illustrated in FIG. 23 is a preferred embodiment of the exhalation port 100 in which the shroud 116 includes four recessed strips 125 alternating with four strips 128. The recesses strips 125 can have a depth of about 0.6 mm. Each recessed strip 125 can span about 60° of a circle formed by the wall of the shroud 116. Each ridge 128 can span about 30° of the circle formed by the wall of the shroud 116. As shown in FIG. 23, the recessed strips 125 are equally spaced on the circle formed by the wall of the shroud 116. The shroud can further include four notches 118, having a rounded spacing between the notches 118. The notches 118 can be spaced equally around the outside surface 120 of the shroud 116, and the dimensions of the notches 118 are substantially equal to the spacing dimensions between the notches 118. As shown in FIG. 23, a center line of the notches 118 and a center line of the recessed strips 125 can be coincident so that the notches 118 align with the recessed strips 125. As shown in FIG. 23, a center line of the spacing between the notches 118 can also be coincident with a center line of the ridges 128. Having four 60°×0.6 mm recessed strips 125 equally spaced on the circle formed by the wall of the shroud 116 and aligned with the notches 118 can advantageously provide increased area for airflow, shorter leak paths 126, and reduced air flow resistance, as well as stable connection between the shroud 116 and the filter 170, 172.

In embodiments of the exhalation port connected to the external filters 170, 172, the flow resistance across the filter 170, 172 is configured to be small such that most of the exhaled gases still exit from the filter 170, 172 instead of through the leak paths 126. In one embodiment, about 75% of the exhaled gases exit from the filter 170, 172. The flow resistance of the exhaled gases through the leak paths 126 can be adjusted by adjusting how far the filter 170, 172 is plugged in from the outer surface 120 toward the centre portion 104. The filter 170, 172 can be plugged into the shroud 116 with a distance just enough to allow the filter 170, 172 to be coupled with the shroud 116. The leak paths 126 can therefore be short and have low flow resistance for the exhaled gases to leave from the leak paths 126. In some situations, a higher percentage of the exhaled gases is required to be filtered, such as during a pandemic. The filter 170, 172 can then be plugged in as close to the centre portion 104 as possible, resulting in the longer leak paths 126 and higher flow resistance for the exhaled gases to leave from the leak paths. More exhaled gases can thus leave from the filter 170, 172. In some embodiments, the leak paths 126 are located so as to not align with the notches 118 so that more exhaled gases exit through the filter 170, 172 instead of the leak paths 126.

In some embodiments, the exhalation port 100 further includes a proprietary filter connection adapter (not shown). The filter connection adapter can be configured to removably connect the shroud 116 to the filter 170, 172 so as block the leak paths 126 and direct more exhaled gases to exit through the filter 170, 172. In one embodiment, the filter connection adapter comprises alternating patterns of recesses and ridges that are complementary to the alternating ridges 128 and recessed strips 125 of the shroud 116 so that the leak paths 126 can be substantially blocked by the filter connection adapter. In other embodiments, the filter connection adapter can have pliant or flexible materials that assume the shape of the leak paths 126 when the filter connection adapter is connected between the shroud 116 and the filter 170, 172.

Figure 10A:
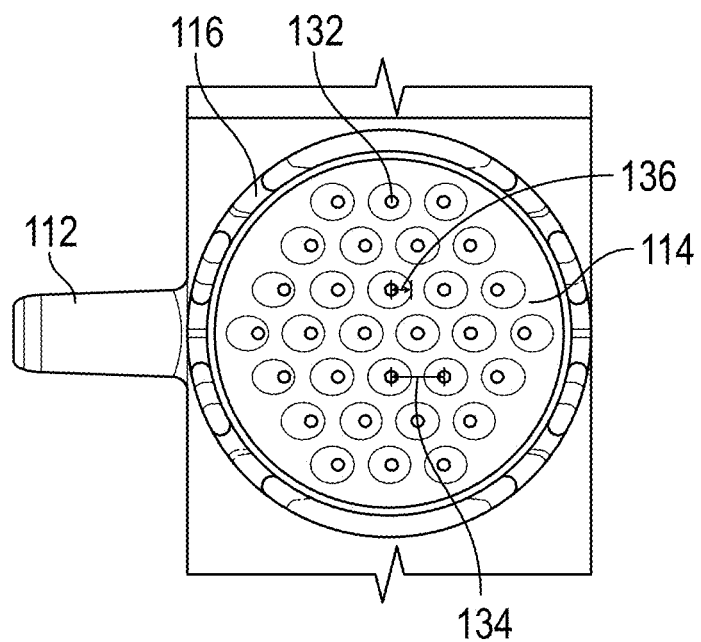
FIGS. 10A and 10B are front and cross-sectional views, respectively, of hole designs for use in an exhalation port in accordance with an embodiment of the present disclosure.
Figure 10B:
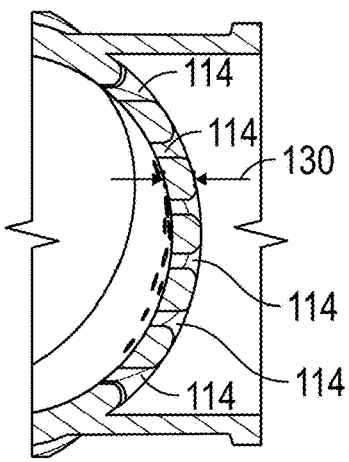
Figure 11A:
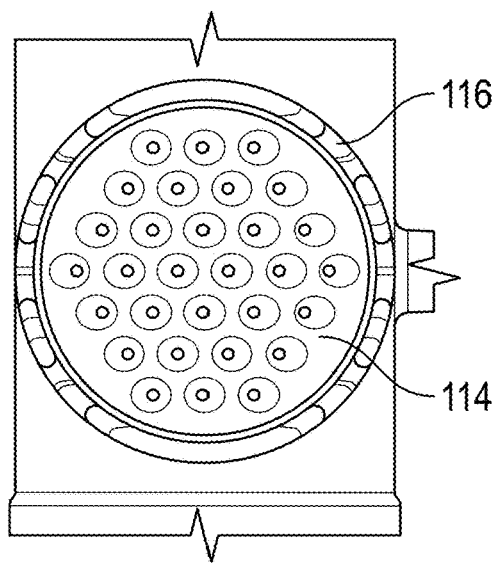
FIGS. 11A and 11B are front views of triangular hole-grid patterns in accordance with an embodiment of the present disclosure.
Figure 11B:
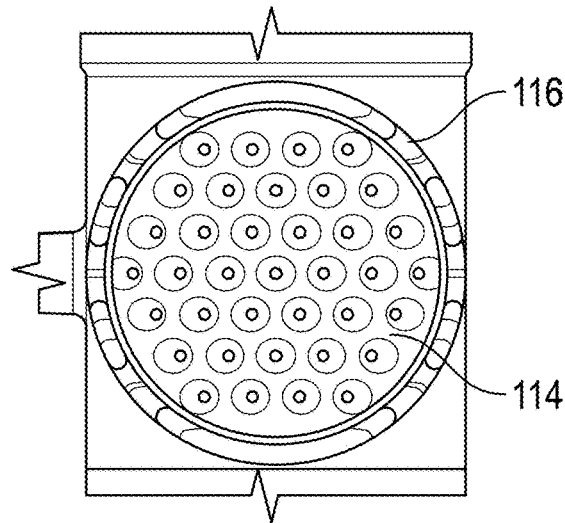

FIGS. 10A-10B illustrate various aspects of the vent holes 114, or openings 114. The vent holes 114, or openings 114, provide a passageway for the patient's exhaled gases to exit the breathing circuit. Noise created as the exhaled gases exit the breathing circuit through the exhalation port 100 can be a source of distraction for patients. Advantageously, the holes 114 are formed and arranged so as to reduce the noise of the exhaled gases. As illustrated in FIGS. 10A and 10B, preferably, a depth 130 of a hole 114 is at least two times an inner diameter 132 of the hole 114. This ratio helps to reduce noise. In an embodiment, preferably, the hole depth 130 is approximately 1.5 mm. Additionally, a pitch distance 134—the distance between centers of two adjacent holes 114—is at least four times the inner diameter 132 of the hole 114. Again, this ratio helps to reduce noise. According to an embodiment, the pitch distance 134 is approximately 3 mm. Preferably, the holes 114 all have the same inner diameter 132. In certain embodiments, the holes 114 preferably have an inner diameter 132 between approximately 0.4 mm and approximately 1.0 mm. In certain preferred embodiments, the holes 114 are tapered, having an external radius 136 at the outer surface of the hole 114. Preferably, the outer radius 136 is between approximately 0.4 mm and approximately 0.75 mm. Thus, in a preferred embodiment, the hole depth 130 is approximately 1.5 mm, the pitch distance 134 between holes 114 is approximately 3 mm, the inner diameter 132 of the hole 114 is approximately 0.75 mm, and the external radius 136 of the hole is approximately 0.7 mm. In another preferred embodiment, the inner diameter 132 of an opening 114 is approximately 0.9 mm, the depth 130 of the opening 114 is at least approximately 1.8 mm, the pitch distance 134 between adjacent openings 114 is at least approximately 3.6 mm, and the external radius 136 of the opening 114 is approximately 0.75 mm.

Figure 12A:
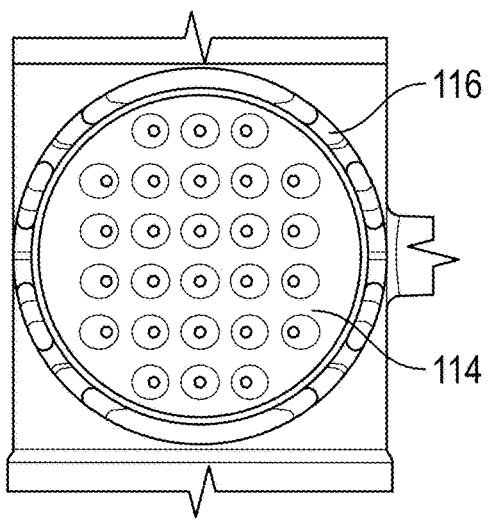
FIGS. 12A and 12B are front views of square hole-grid patterns in accordance with an embodiment of the present disclosure.
Figure 12B:
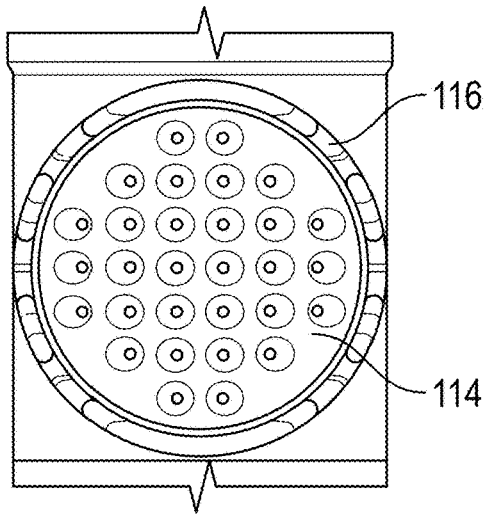
Figure 13A:
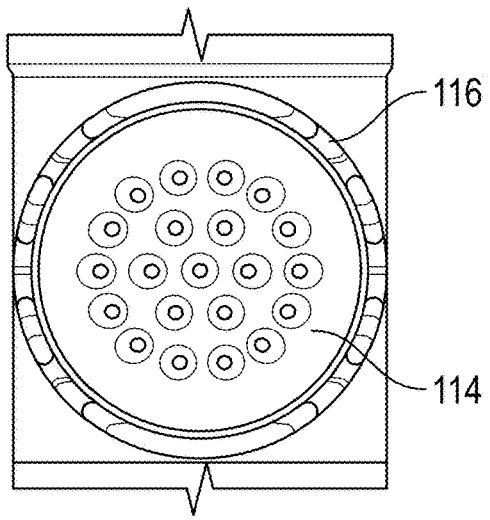
FIGS. 13A-13D are front views of circular hole-grid patterns in accordance with an embodiment of the present disclosure.
Figure 13B:
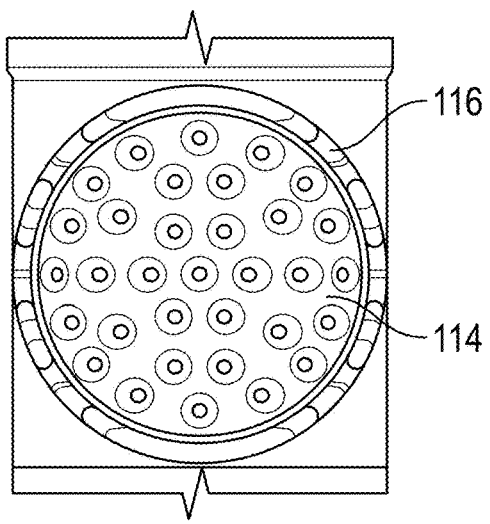
Figure 13C:
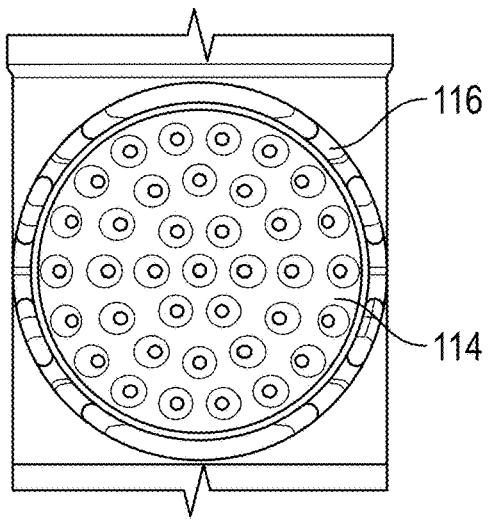
Figure 13D:
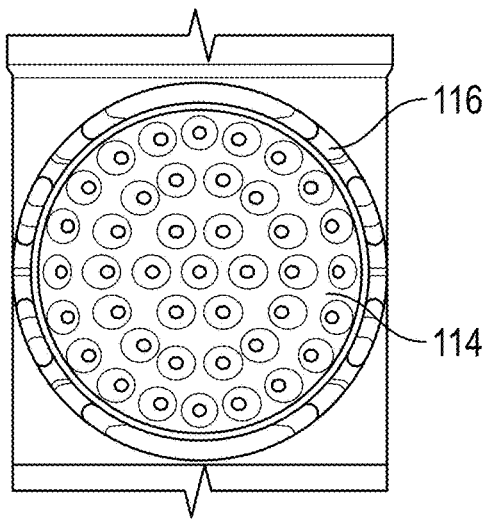

In a preferred embodiment, the vent holes 114 are in a square arrangement including 21 holes in which all holes 114 are aligned with each other. In this embodiment, not all of the holes 114 have a consistent pitch distance 134 between adjacent holes 114. As illustrated in FIGS. 11A-11B, 12A-12B, and 13A-13D, various patterns and arrangements 11A and 11B illustrate triangular, equal-distance vent hole 114 grid patterns having 30 and 37 holes 114, respectively. FIGS. 12A and 12B illustrate square vent hole 114 grid patterns having 26 and 30 holes, respectively. FIGS. 13A-13D illustrate circular, ring-shaped vent hole 114 patterns having 21, 33, 37, and 41 holes 114, respectively.

Figure 14A:
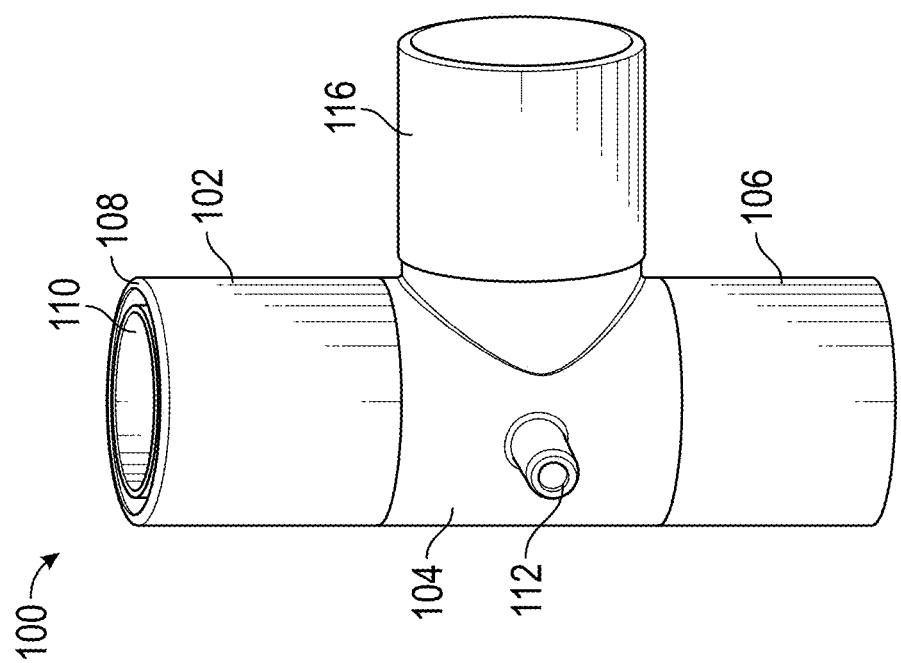
Figure 14D:
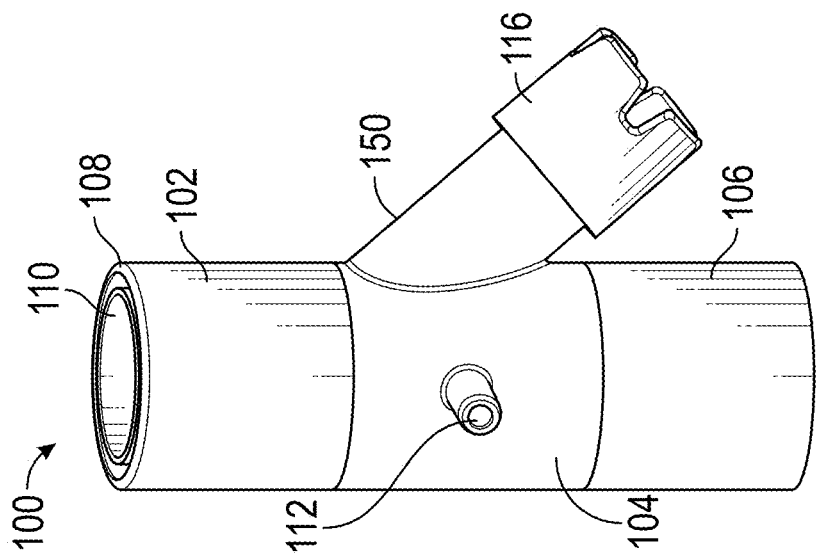
Figure 14C:
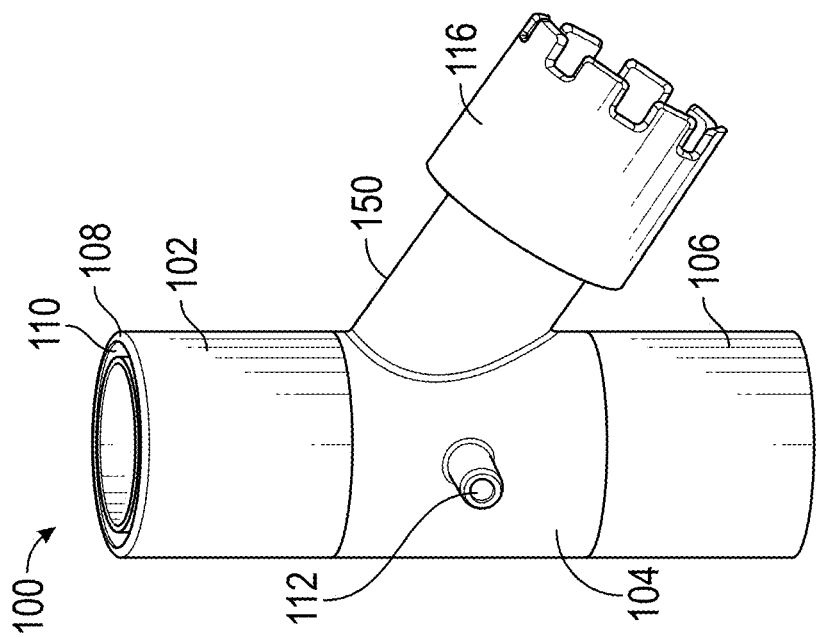

FIGS. 14A-14C illustrate various alternative embodiments of the exhalation port 100, demonstrating several of the features of the present disclosure. FIG. 14A illustrates an embodiment of the exhalation port 100 in which the shroud 116 is planar, i.e., the shroud 116 has no notches 118 or slots 124 within the wall 122 of the shroud 116. In this embodiment, the shroud 116 projects straight outward, i.e., normal to the longitudinal axis of the exhalation port 100. The shroud 116 includes a 22 mm male taper to interface with an external filter 170.

As discussed above, FIG. 14B illustrates a an embodiment of the exhalation port 100 in which the shroud 116 includes notches 118 that are spaced equally around the outside surface 120 of the shroud 116, and the dimensions of the notches 118 are substantially equal to the spacing dimensions 119 between the notches 118. Additionally, the elongate body 101 is at a reduced length to provide a more compact exhalation port 100. The shroud 116 includes a 22 mm male taper to interface with an external filter 170.

FIGS. 14C and 14D illustrate alternative embodiments of the exhalation port 100 featuring an angled connection 150 for the shroud 116. Advantageously, the angled connection 150 directs exhaled gasses away from the caregiver and the patient. The angled connection 150 can be at any angle, including 90 degrees from the elongate body 101. In some embodiments the angled connection 150 can be at an angle between approximately 30 degrees and 45 degrees or at an angle between approximately 120 degrees and 135 degrees, depending on the orientation from the patient interface. The shroud 116 illustrated in FIG. 14C includes a 22 mm male taper to interface with an external filter 170. The shroud 116 illustrated in FIG. 14D includes a 15 mm male taper to interface with an external filter 172.

Figure 15A:
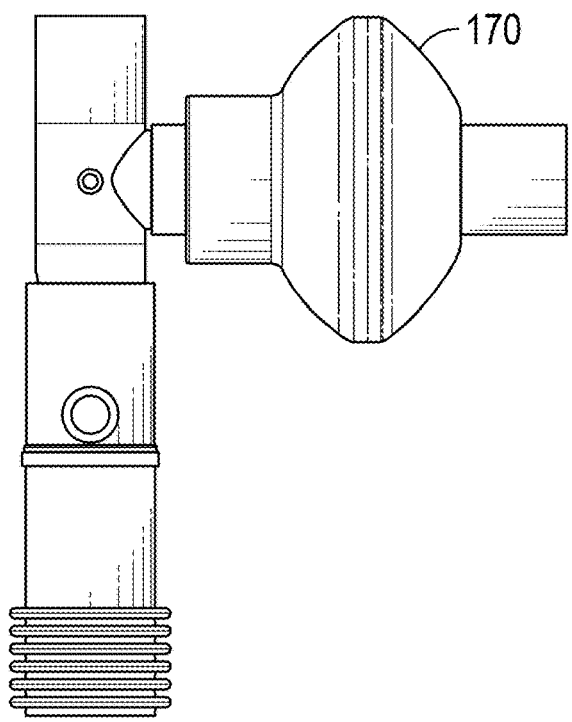
FIGS. 15A-15D are side views of exhalation ports to which external filters are attached in accordance with embodiments of the present disclosure.
Figure 15B:
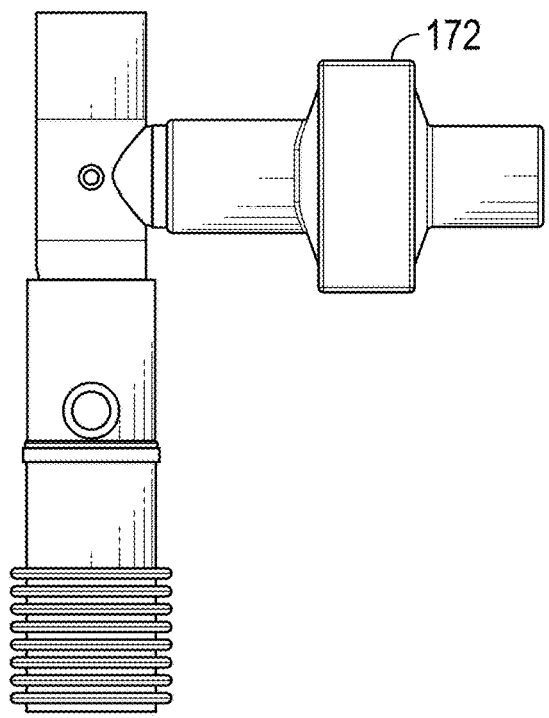

FIGS. 15A-15D illustrate various alternative embodiments of the exhalation port 100 to which an external filter 170,172 is attached. As previously described, the external filter 170, 172 protects the surrounding environment from being exposed to infectious agents that can be present in the patient's exhaled gases. FIGS. 15A and 15B show two configurations in which the external filters 170, 172 are attached to shrouds 116 which extend outward approximately normal (i.e., at a 90 degree angle) from the elongate body 101 of the exhalation port 100. In FIGS. 15A and 15B, the external filters 170, 172 have 22 mm female tapers with which to mate with a 22 mm male taper of the shroud 116 to establish connection between the external filters 170, 172 and the shroud 116 of the exhalation port 100.

Figure 15C:
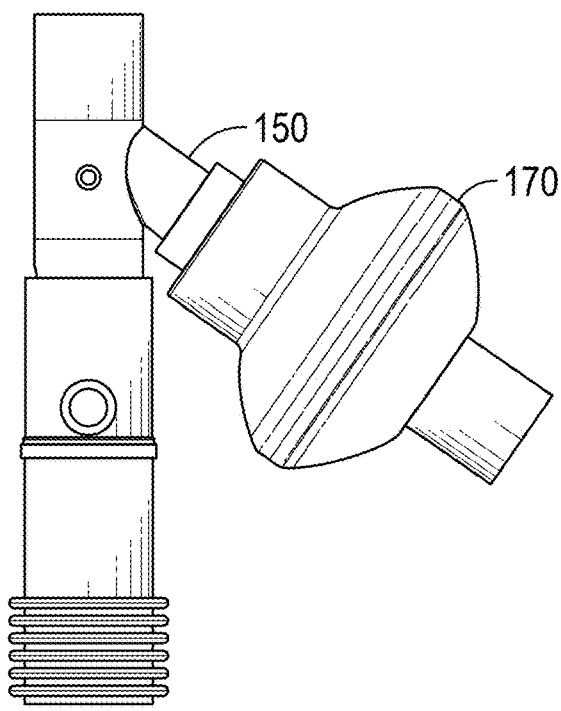
Figure 15D:
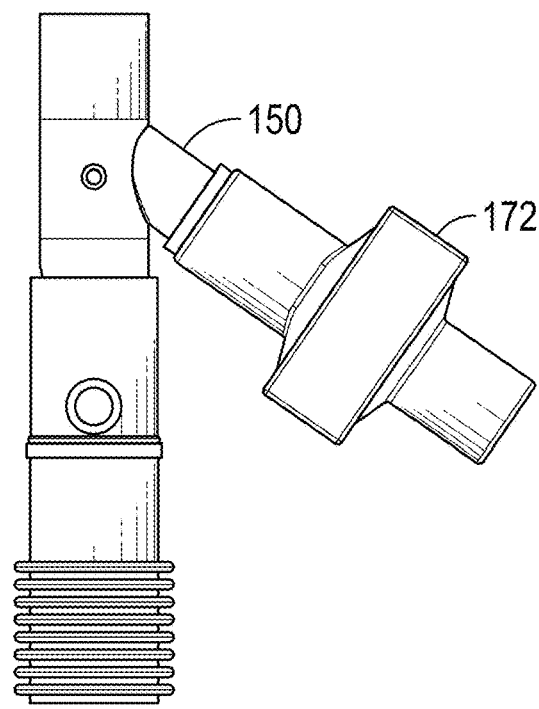

FIGS. 15C and 15D show two configurations in which the external filters 170, 172 are attached to shrouds 116 which extend outward from the elongate body 101 of the exhalation port 100 at an angled connection 150. The external filters 170, 172 have 22 mm female tapers with which to mate with a 22 mm male taper of the shroud 116 to establish connection between the external filter 170 and the shroud 116 of the exhalation port 100. Of course, a skilled artisan will appreciate that many types, forms and formats of external filters 170, 172 can be used with the embodiments of the present disclosure.

Figure 16A:
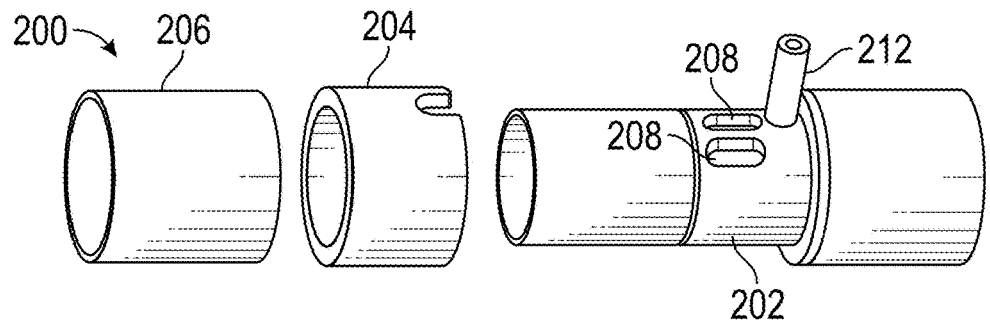
FIGS. 16A and 16B are exploded and collapsed front views, respectively, of an integrated filter/diffuser in accordance with an embodiment of the present disclosure.
Figure 16B:
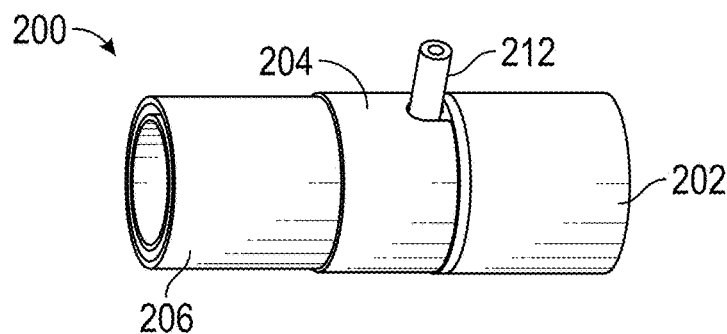

Referring now to FIGS. 16A and 16B, an embodiment of the disclosed exhalation port 200 includes and integrated filter/diffuser. FIG. 16A shows an exploded view of the exhalation port 200. A main body 202 provides the structure onto which a sintered diffuser 204 and a top portion 206 are assembled to form the exhalation port 200. The main body 202 includes a pressure line port 212 to couple with a pressure sampling line that connects to the noninvasive ventilator or gases source. When the pressure line port 212 is not in use, it may be closed off with a cap (not shown). The main body 202 also includes exhalation vents 208 through which the patient's exhaled gases may pass. The sintered filter/diffuser 204 is made of a plastic material that permits airflow to pass through it. Thus, in operation, the exhaled gases exit through the exhalation vents 208 of the main body 202 into and through the sintered filter/diffuser 204 to exit the breathing circuit and enter the surrounding environment. The top portion 206 fits over the main body 202 and adjacent the sintered filter/diffuser 204, as illustrated FIG. 16B in which the exhalation port 200 is assembled. Advantageously, the exhalation port 200 is effective at reducing noise and draft created by the exhalation of a patient's respiratory gases and filtering the exhaled gases.

Figure 17A:
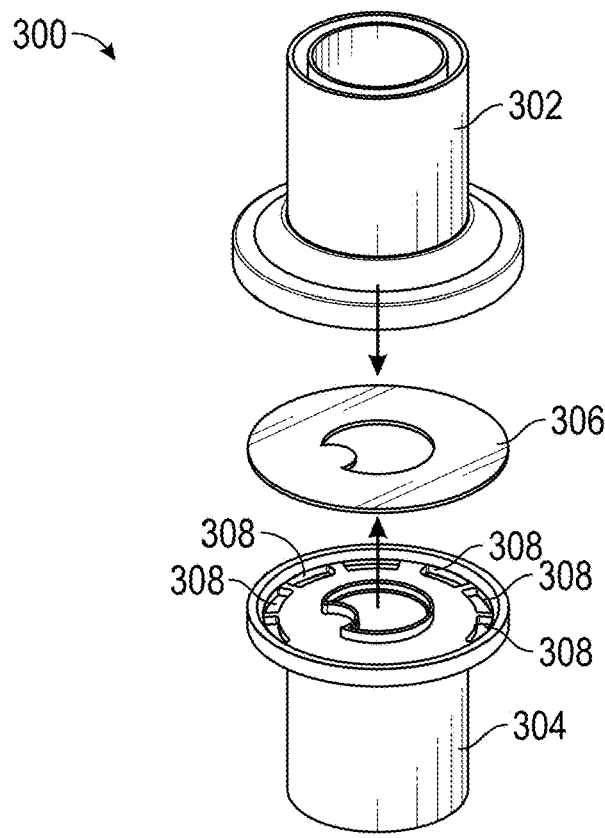
FIGS. 17A-17C are exploded, assembled, and cross-sectional views, respectively, of an integrated filter/diffuser in accordance with an embodiment of the present disclosure.
Figure 17B:
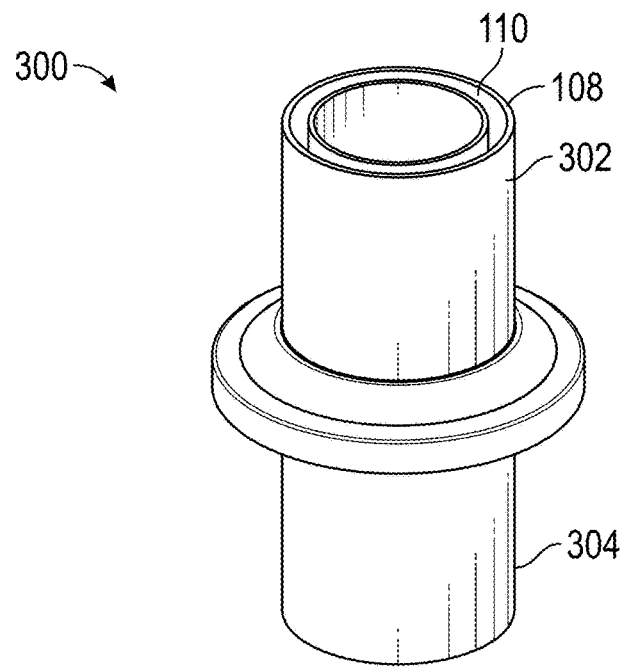
Figure 17C:
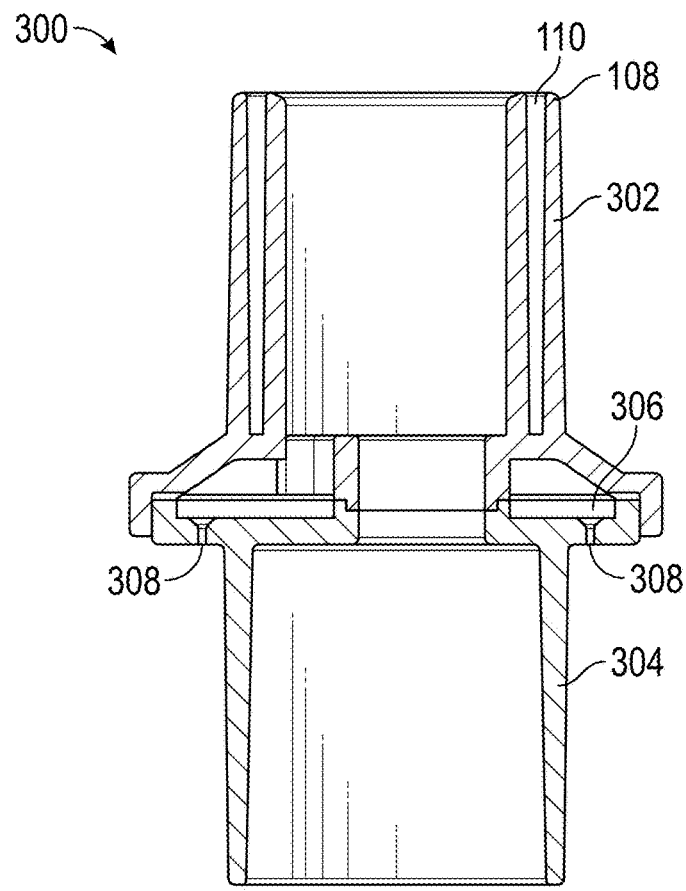

FIGS. 17A-17C illustrate another embodiment of an exhalation port 300 that includes and integrated filter. FIG. 17A shows the exhalation port 300 in an exploded perspective view. The exhalation port 300 includes a top half 302, a bottom half 304, and a filter media 306. The bottom half 304 also includes exhalation vents 308 through which filtered exhaled gases may pass from the breathing circuit to the surrounding environment. In assembly, the two halves 302 and 304 can be ultrasonically welded together with the filter media 306 positioned between the two halves 302 and 304. The assembled exhalation port 300 operates in-line, in the breathing circuit. The patient's exhaled gases pass through the filter media 306 and are channelled through the port 300 to the exhalation vents 308. Advantageously, the exhalation port 300 filters infectious material from the exhaled gases via an in-line system, thereby avoiding the need to add structure (such as a shroud 116) to accommodate an external filter 170, 172.

Figure 18A:
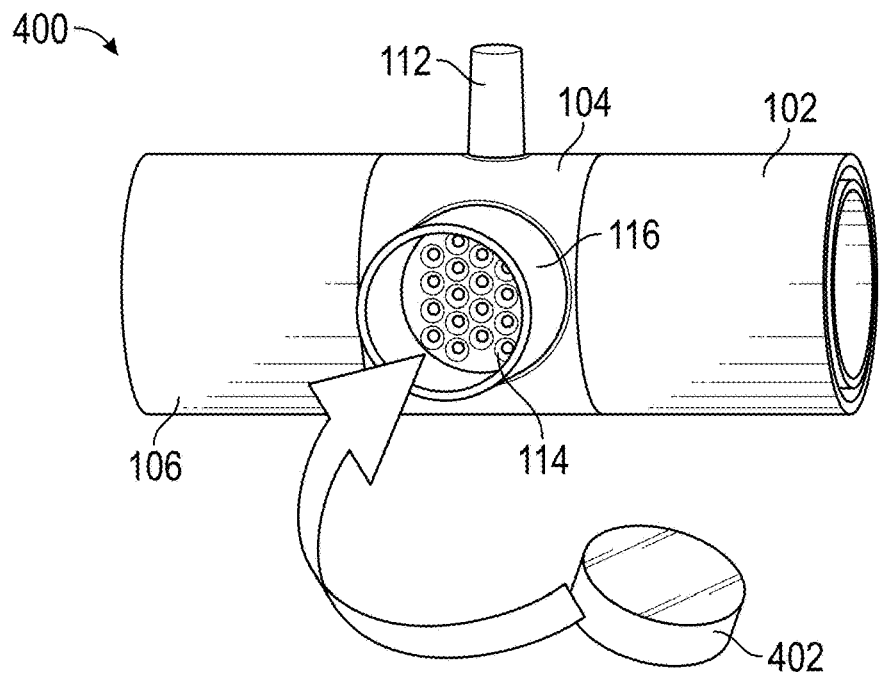
FIGS. 18A and 18B are perspective and cross-sectional views, respectively, of an integrated filter/diffuser in accordance with an embodiment of the present disclosure.
Figure 18B:
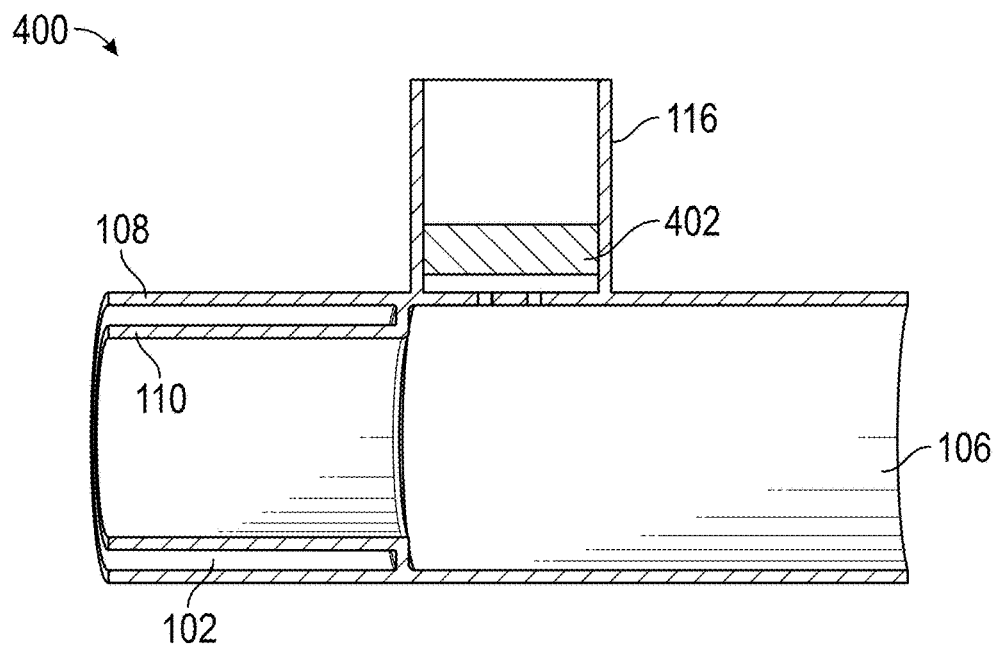

FIGS. 18A-18B illustrate yet another embodiment of an exhalation port 400 in which a removable filter/diffuser 402, which is a disk or cap, is inserted within the shroud 116. The removable filter/diffuser 402 can be made of sintered plastic, foam, or fabric materials that can reduce the noise associated with exhalation of respiratory gases and permit airflow to pass through it. Thus, in operation, the exhaled gases exit through the vent holes 114 into and through the sintered filter/diffuser 402 to exit the breathing circuit and enter the surrounding environment. Advantageously, the exhalation port 400 provides noise reduction of exhalation gases being expelled from the breathing circuit without increasing adding to the size or volume of the exhalation port 400. The exhalation port 400 can also filter the exhaled gases.

Figure 19A:
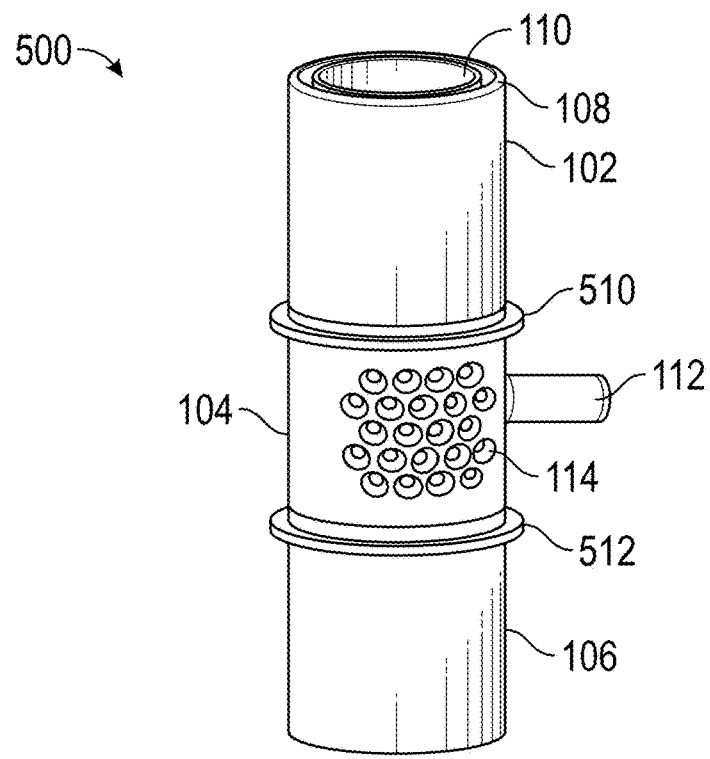
FIGS. 19A-19C are perspective views of a hinged filter taper adapter in accordance with an embodiment of the present disclosure.
Figure 19B:
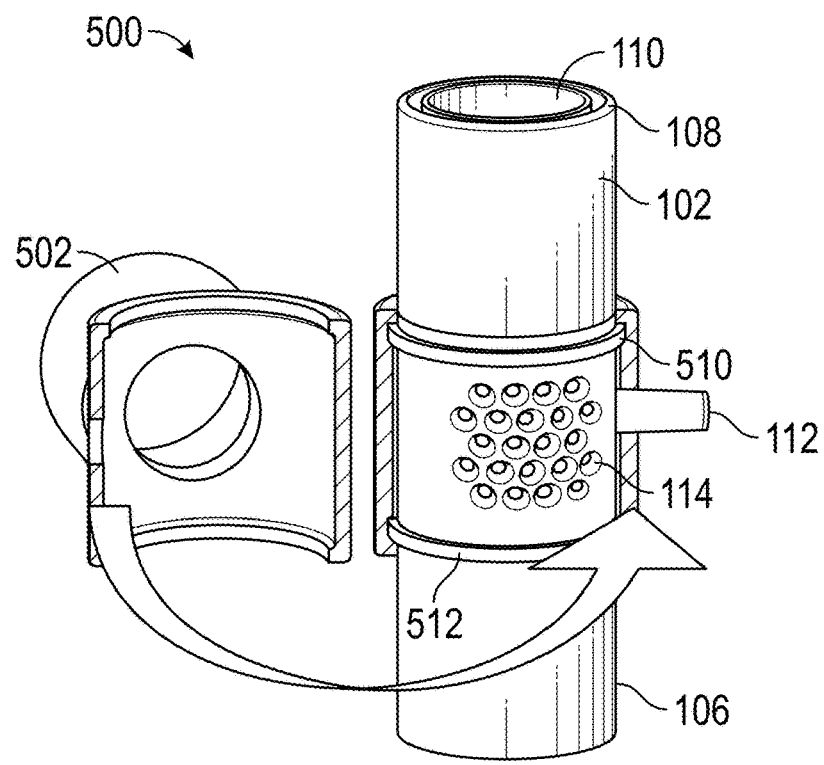
Figure 19C:
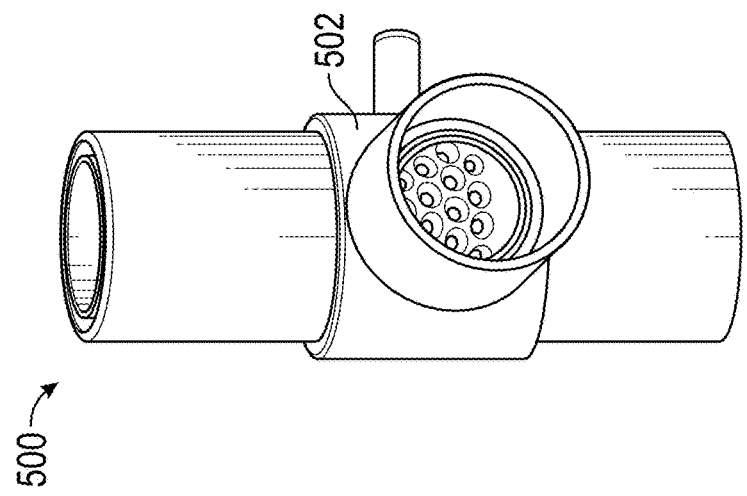

FIGS. 19A-19C illustrate another embodiment of an exhalation port 500 in which a hinged shroud 502 is optional and separately attachable to the exhalation port 500. The exhalation port 500 includes most of the elements described with respect to the embodiment of exhalation port 100, including a top portion 102, a center portion 104, and a bottom portion 106, a 22 mm male taper 108, a 15 mm female taper 110, a pressure line port 112, and a plurality of vent holes 114, or openings 114. The exhalation port 500 also includes an upper ledge 510 and a lower ledge 512 which are used to attach the hinged shroud 502 to the exhalation port 500. As illustrated in FIG. 19B, the hinged shroud 502 includes two halves, which may be connected by a hinge (not shown for ease of illustration), which are attached to the exhalation port 500. Once assembled, as illustrated in FIG. 19C, the hinged shroud 502 is configured to attach to an external filter 170 to the exhalation port 500 and to reduce the entrainment of ambient air within the exhalation stream. The hinged shroud 502 reduces draft by preventing ambient air from being sucked up into the exhalation air stream. Advantageously, the exhalation port 500 provides a simplified form factor for use in circumstances where it is not desired to employ an external filter 170 because, for example, the patient does not pose a risk of infection to care providers or others in proximity of the patient's exhaled gases. If the patient subsequently presents a risk of infection, then the hinged shroud 502 can be attached to the exhalation port 500 to enable attachment of an external filter 170.

Figure 20B:
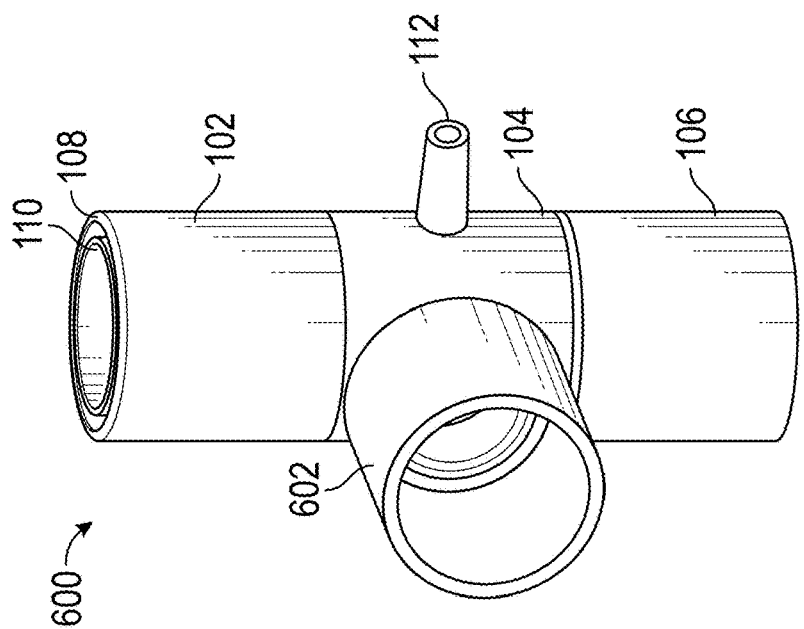
FIGS. 20A and 20B are perspective views of a click-on attachment for a filter taper adapter in accordance with an embodiment of the present disclosure.
Figure 20A:
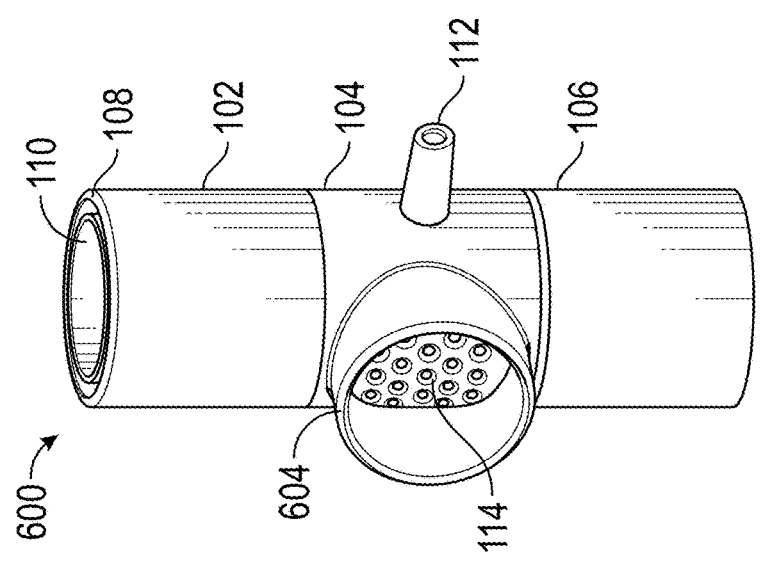

FIGS. 20A-20B illustrate another embodiment of an exhalation port 600 in which a removable shroud 602 is optional and separately attachable to the exhalation port 600. In this embodiment, a shroud connector 604 surrounds the vent holes 114. The shroud connector 604 is configured to receive a 22 mm female taper of the removable shroud 602. As illustrated in FIG. 20B, the removable shroud 602 mates with the shroud connector 604 to secure the removable shroud 602 in place. Methods of mating the shroud 602 to the shroud connector 604 can include, among others, snug-fit and click-on connections, as well as standard medical 22 mm and 15*mm* taper connections. Once secured, the removable shroud 602 is configured to attach to an external filter 170, 172 to the exhalation port 600 and to reduce the entrainment of ambient air within the exhalation stream.

Various embodiments of the disclosed exhalation port have been described herein. Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

Where, in the foregoing description reference has been made to integers or components having known equivalents thereof, those integers are herein incorporated as if individually set forth.

Reference to any prior art in this specification is not, and should not be taken as an acknowledgement or any form of suggestion that that prior art forms part of the common general knowledge in the field of endeavor in any country in the world.

Certain features, aspects and advantages of some configurations of the present disclosure have been described with reference to use by a patient or user. However, certain features, aspects and advantages of the use of the exhalation port as described may be advantageously practiced by other people on behalf of the patient, including medical professionals, medical device dealers, or medical device providers. Certain features, aspects and advantages of the methods and apparatus of the present disclosure may be equally applied to usage by other people.

Although the present disclosure has been described in terms of certain embodiments, other embodiments apparent to those of ordinary skill in the art also are within the scope of this disclosure. Thus, various changes and modifications may be made without departing from the spirit and scope of the present disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. An exhalation port for respiratory therapy comprising:
an elongate body, said elongate body being hollow and defining a lumen configured to carry a flow of gases;
a center portion;
a plurality of holes arranged on a portion of the elongate body, the plurality of holes configured to vent gases through the elongate body;
a pressure port extending outward from the elongate body, the pressure port configured to couple with a pressure sampling line that connects to a noninvasive ventilator;
a shroud configured to be removably attached to the elongate body, the shroud configured to extend from the elongate body and surround one or more of the plurality of holes when attached to the elongate body, the shroud comprising a wall and an outer surface;
wherein a plurality of alternating recessed strips and ridges are provided on the wall of the shroud, the plurality of alternating recessed strips and the ridges extending from the outer surface of the shroud toward the center portion, and
wherein the exhalation port is configured to removably connect in-line with a circuit for delivering the flow of gases to a patient.

2. The exhalation port of claim 1, wherein the wall comprises four recessed strips alternating with four ridges.

3. The exhalation port of claim 2, wherein the four recessed strips are substantially equally spaced around a circumference of the shroud.

4. The exhalation port of claim 1, wherein the plurality of alternating recessed strips and ridges reach the center portion of the exhalation port.

5. The exhalation port of claim 1, wherein the plurality of alternating recessed strips and ridges stop between the outer surface of the shroud and the center portion of the exhalation port.

6. The exhalation port of claim 1, wherein the shroud extends outward from the elongate body.

7. The exhalation port of claim 6, wherein the shroud extends outward from the elongate body in a substantially annular form.

8. The exhalation port of claim 1, wherein the outer surface has a 22 mm taper or a 15 mm taper configured to connect with a filter.

9. The exhalation port of claim 1, comprising a plurality of notches spaced around the outer surface of the shroud.

10. The exhalation port of claim 9, wherein the plurality of notches are spaced equally around the outer surface of the shroud.

11. The exhalation port of claim 10, wherein each of the plurality of notches comprises a notch dimension and a spacing dimension, the notch dimension being substantially equal to or greater than the spacing dimension.

12. The exhalation port of claim 10, wherein a center line of the notches and a center line of the recessed strips are coincident such that the plurality of notches align with the recessed strips.

13. The exhalation port of claim 10, wherein a center line of the spacing between the notches and a center line of the ridges are coincident such that the notches align with the ridges.

14. The exhalation port of claim 1, wherein the elongate body further comprises a first end, wherein the first end of the elongate body comprises a 22 mm male taper and a 15 mm female taper nested within the 22 mm taper.

15. The exhalation port of claim 1, wherein the shroud is hingedly attached to the elongate body.

16. The exhalation port of claim 1, further comprising a filter, wherein the filter is a diffuser that is configured to be removably placed in the shroud.

* * * * *

UNITED STATES PATENT AND TRADEMARK OFFICE
CERTIFICATE OF CORRECTION

PATENT NO. : 11,617,848 B2
APPLICATION NO. : 16/810751
DATED : April 4, 2023
INVENTOR(S) : Katie Fyfe et al.

It is certified that error appears in the above-identified patent and that said Letters Patent is hereby corrected as shown below:

In the Specification

In Column 1 at approximately Line 10, delete "No." and insert --"Nos.--.

In Column 11 at Line 34, after "arrangements" insert --of holes 114 can be used to realize the exhalation port 100 of the present disclosure. FIGS.--.

Signed and Sealed this
Fifth Day of September, 2023

Katherine Kelly Vidal
*Director of the United States Patent and Trademark Office*